(12) United States Patent
Baskar et al.

(10) Patent No.: US 10,190,084 B2
(45) Date of Patent: Jan. 29, 2019

(54) METHOD OF CULTURING EUKARYOTIC CELLS

(71) Applicant: Genentech, Inc., South San Francisco, CA (US)

(72) Inventors: Dinesh Baskar, Bangalore (IN); Jenny Hsiung, Mountain View, CA (US); Woon-Lam Susan Leung, San Mateo, CA (US); Inn H. Yuk, Berkeley, CA (US)

(73) Assignee: Genentech, Inc., South San Francisco, CA (US)

( * ) Notice: Subject to any disclaimer, the term of this patent is extended or adjusted under 35 U.S.C. 154(b) by 0 days.

(21) Appl. No.: 14/480,366

(22) Filed: Sep. 8, 2014

(65) Prior Publication Data

US 2015/0210971 A1    Jul. 30, 2015

Related U.S. Application Data

(63) Continuation of application No. 13/383,829, filed as application No. PCT/US2010/041082 on Jul. 6, 2010, now abandoned.

(60) Provisional application No. 61/223,313, filed on Jul. 6, 2009.

(51) Int. Cl.
| | |
|---|---|
| *C12N 5/071* | (2010.01) |
| *C12M 3/00* | (2006.01) |
| *C12M 1/00* | (2006.01) |
| *C12M 3/06* | (2006.01) |
| *C12M 1/34* | (2006.01) |
| *C12M 1/36* | (2006.01) |
| *C12N 5/00* | (2006.01) |

(52) U.S. Cl.
CPC ............ *C12M 23/14* (2013.01); *C12M 23/28* (2013.01); *C12M 27/16* (2013.01); *C12M 29/10* (2013.01); *C12M 29/20* (2013.01); *C12M 41/12* (2013.01); *C12M 41/26* (2013.01); *C12M 41/32* (2013.01); *C12M 41/48* (2013.01); *C12N 5/0018* (2013.01); *C12N 2500/05* (2013.01)

(58) Field of Classification Search
None
See application file for complete search history.

(56) References Cited

U.S. PATENT DOCUMENTS

| | | |
|---|---|---|
| 3,941,662 A | 3/1976 | Munder et al. |
| 4,142,940 A | 3/1979 | Modolell et al. |
| 4,680,267 A | 7/1987 | Eppstein et al. |
| 6,190,913 B1 | 2/2001 | Singh |
| 6,544,788 B2 * | 4/2003 | Singh ................ B01F 11/0017 435/297.1 |
| 2003/0036192 A1 | 2/2003 | Singh |
| 2006/0013063 A1 * | 1/2006 | Singh ................ B01F 11/0017 366/239 |
| 2006/0019385 A1 | 1/2006 | Smith et al. |
| 2006/0196501 A1 | 9/2006 | Bibbo et al. |
| 2007/0026516 A1 | 2/2007 | Martin et al. |
| 2009/0095192 A1 | 4/2009 | Roop |
| 2012/0329151 A1 | 12/2012 | Baskar et al. |
| 2015/0368602 A1 | 12/2015 | Galliher et al. |

FOREIGN PATENT DOCUMENTS

| | | | |
|---|---|---|---|
| DE | 3606449 | 9/1986 | |
| EP | 0147975 | 7/1985 | |
| EP | 0200226 | 11/1986 | |
| EP | 0567738 A2 * | 11/1993 | ............ C12M 41/00 |
| EP | 2020433 | 2/2009 | |
| JP | S60-141286 A | 7/1985 | |
| JP | S61-202684 A | 9/1986 | |
| JP | H03-010679 A | 1/1991 | |
| JP | 2008-501347 A | 1/2008 | |
| JP | 2009-072182 A | 4/2009 | |
| WO | 2005/118771 | 12/2005 | |

OTHER PUBLICATIONS

Pierce et al. "Scalability of a disposable bioreactor from 25L-500L run in perfusion mode with a CHO-based cell line: a tech review", Bioprocessing Journal Jul./Aug.: 51-56, 2004.*
Kimura et al. "Effects of elevated pCO2 and/or osmolality on the growth and recombinant tPA production of CHO cells", Biotechnology and Bioengineering 52(1): 152-160, 1996.*
Frison et al. "Fed-batch process for monoclonal antibody production", Genetic Engineering News 22(11): 64-66, 2002.*
Cell Culture Protocol: 'Cultivation of Human Embryonic Kidney (HEK) 293 cells in Suspension', Protocol #03-10 (GE Healthcare), Dec. 2003, http://cercell.com/wp-content/uploads/GE-instruction-wavebags.pdf, (in 3 pages) ( Dec. 2003).
DE 3606449 English Abstract, p. 1.
Dezengotita et al., "Effects of CO2 and osmolality on hybridoma cells: growth, metabolism and monoclonal antibody production" Cytotechnology, 28:213-227 ( 1998).
Durocher et al. et al., "High-level and high-throughput recombinant protein production by transient transfection of suspension-growing human 293-EBNA1 cells" Nucleic Acids Res 30(2):E9 ( 2002).
Freshney, Culture of Animal Cells: A Manual of Basic Technique, 5th Edition, John Wiley & Sons, Inc., 115-128 ( 2005).
Frison et al., "Fed-batch process development for monoclonal antibody production with cellferm-pro®" Genetic Engineering News, vol. 22, No. 11, (Published: Jun. 1, 2002).
International Search Report of PCT/US2010/041082, Pub. No. WO 2011/005773, pp. 1-6 ( Jan. 13, 2011).
Translation of Mexican Office Action issued in Mexican Patent Application No. MX/a/2012/000354, in 4 pages (Date of Translation: Aug. 2, 2013).

(Continued)

*Primary Examiner* — Emily A Cordas
(74) *Attorney, Agent, or Firm* — Morrison & Foerster LLP

(57) ABSTRACT

An apparatus and method to maintain pH within a range conducive for cell growth in a bicarbonate-containing cell culture system without the addition of base. The method relies on the gas transfer characteristics of the bioreactor system to modulate the $CO_2$ transfer to and from the cell culture such that the pH of the cell culture can be maintained within a desired range.

16 Claims, 18 Drawing Sheets

(56) References Cited

OTHER PUBLICATIONS

Wave Bioreactor System 500/1000EH Operator Manual, GE Healthcare Feb. 13, 2009, https://www.gelifesciences.com/gehels_images/GELS/Related%20Content/Files/1314774443672/litdoc87450028AD_20110831121032.pdf, (in 149 pages) ( Feb. 13, 2009).
Written Opinion issued in Singaporean Patent Application No. 201200120-2, in 7 pages (dated: Apr. 16, 2014).
Freshney, R. I., *Culture of Animal Cells: a Manual of Basic Technique*, "Carbon Dioxide and Carbonate", 4th edition, Beijing, China: Science Press, 99-101 (2004), with English Translation in 3 pgs.
Bleckwenn et al., "Large-Scale Cell Culture" Current Protocols in Immunology ( Suppl 59, Annex 1U):A.1U.1-A.1U.44 ( 2004).
Chartrain et al., "Development and Production of Commercial Therapeutic Monoclonal Antibodies in Mammalian Cell Expression Systems: An Overview of the Current Upstream Technologies" Current Pharmaceutical Biotechnology 9:447-467 ( 2008).
Weber et al., "Optimisation of protein expression and establishment of the Wave Bioreactor for Baculovirus/insect cell culture" Cytotechnology 38:77-85 ( 2002).
Yuk et al., "Overcoming Challenges in WAVE Bioreactors Without Feedback Controls for pH and Dissolved Oxygen," *Biotechnol. Prog.* 27(5):1397-1406 (2011).
International Preliminary Report on Patentability, dated Jan. 10, 2012 for PCT Application No. PCT/US2010/041082, filed Jul. 6, 2010, 16 pages.
Written Opinion of the International Searching Authority, dated Dec. 14, 2011, for PCT Application No. PCT/US2010/041082, filed Jul. 6, 2010, 15 pages.
Cronin et al. "Production of Selenomethionyl-Derivatized Proteins in Baculovirus-Infected Insect Cells," *Protein Sci.* 6:2023-2029, (2007).
Dezengotita et al. "Characterization of Hybridoma Cell Responses to Elevated $pCO^2$ and Osmolality: Intracellular pH, Cell Size, Apoptosis, and Metabolism," *Biotechnol Bioen.* 77(4):369-380, (2002).
Dunn et al. "Oxygen Transfer Coefficients by the Dynamic Model," *J. Appl. Chem. Biotechnol.* 25(9):707-720, (1975).
Haldankar et al. "Serum-Free Suspension Large-Scale Transient Transfection of CHO Cells in WAVE Biorcactors," *Mol. Biotechnol.* 34(2):191-199, (2006).
Johnson et al."Use of the Centritech Lab Centrifuge for Perfusion Culture of Hybridoma Cells in Protein-Free Medium," *Biotech. Prog.* 12(6):855-864, (1996).

Langheinrich et al. "Control of pH in Large-Scale, Free Suspension Animal Cell Bioreactors: Alkali Addition and pH Excursions," *Biotechnol. Bioeng.* 66(3):171-179, (1999).
Lin et al. "Production of tPA in Recombinant CHO Cells Under Oxygen-Limited Conditions," *Biotechnol. Bioeng.* 42(3):339-350, (1993).
Ling et al. "Improvement of Monoclonal Antibody Production in Hybridoma Cells by Dimethyl Sulfoxide," *Biotechnol. Prog.* 19(1):158-162, (2003, e-pub. Nov. 21, 2002).
Link et al. "Bioprocess Development for the Production of a Recombinant MUC1 Fusion Protein Expressed by CHO-K1 Cells in Protein-Free Medium," *J. Biotechnol.* 110(1):51-62, (2004).
Mikola et al. "Evaluation of a Novel Wave Bioreactor® Cellbag for Aerobic Yeast Cultivation," *Bioprocess Biosyst. Eng.* 30:231-241, (2007).
Miller et al. "A Kinetic Analysis of Hybridoma Growth and Metabolism in Batch and Continuous Suspension Culture: Effect of Nutrient Concentration, Dilution Rate, and pH," *Biotechnol. Bioeng.* 32(8):947-965, (1988).
Osman et al. "The Response of GS-NSO Myeloma Cells to pH Shifts and pH Perturbations," *Biotechnol. Bioeng.* 75(1):63-73, (2001).
Osman et al. "The Response of GS-NSO Myeloma Cells to Single and Multiple pH Perturbations," *Biotechnol. Bioeng.* 79(4):398-407, (2002).
Rao et al. "Disposable Bioprocessing: The Future Has Arrived," *Biotechnol. Bioeng.* 102(2):348-356, (2009, e-pub. Nov. 10, 2008).
Restelli et al. "The Effect of Dissolved Oxygen on the Production and Glycosylation Profile Of Recombinant Human Erythropoietin Produced From CHO Cells," *Biotechnol. Bioeng.* 94(3):481-494, (2006, e-pub. Mar. 7, 2006).
Royce et al. "Estimation of Dissolved Carbon Dioxide Concentrations in Aerobic Fermentations," *Aiche J.* 37(11):1680-1686, (1991).
Singh. "Disposable Bioreactor for Cell Culture Using Wave-Induced Agitation," *Cytotechnology* 30:149-158, (1999).
Tang et al. "Perfusion Culture of Hybridoma Cells for Hyperproduction of $IgG_{2a}$ Monoclonal Antibody in A Wave Bioreactor-Perfusion Culture System," *Biotechnol. Prog.* 23(1):255-264, (2007, e-pub. Jan. 19, 2007).
Tang et al. "Modulation and Control of pH," in *Techniques of Culture of Hematopoietic Cell*, Shanxi Science and Technology Press. $1^{st}$. Ed. pp. 58-66, (Oct. 1985). (Brief description of the relevant section can be found in the English translation of the Chinese First Office Action on p. 2).
Chinese First Office Action, English translation dated Nov. 2, 2018, for Chinese Patent Application No. 2016011012418.x, filed Nov. 17, 2016, 8 pages.

* cited by examiner

A

B

D

A

B

D

A

B

A

B

C

D

METHOD OF CULTURING EUKARYOTIC CELLS

CROSS-REFERENCE TO RELATED APPLICATIONS

This application is a continuation of U.S. patent application Ser. No. 13/383,829, filed on Sep. 10, 2012, now abandoned, which is a 371 of International Application No. PCT/US2010/041082, filed on Jul. 6, 2010, which claims benefit of U.S. Provisional Application No. 61/223,313, filed on Jul. 6, 2009, the entire contents of which are incorporated by reference herein in their entireties.

FIELD OF THE INVENTION

The invention relates to an apparatus and method for culturing eukaryotic cells in a bicarbonate-containing medium that allows maintenance of pH of the cell culture without the addition of bases directly to the culture medium.

BACKGROUND OF THE INVENTION

The culturing of cells for cell banking, for production of cell products, such as recombinant protein production is hampered by changing conditions as cells grow. While stainless steel bioreactors are often used for cell production, disposables are increasingly used at all stages in biologics manufacturing (Rao et al., 2009). In upstream processing, disposable bioreactors offer many advantages over their stainless steel counterparts (ranging from reducing cross-contamination risks to cost and time savings). The WAVE BIOREACTOR™ is a well-documented example of disposable upstream technology used for recombinant protein production in the biopharmaceutical industry (Cronin et al., 2007; Haldankar et al., 2006; Ling et al., 2003; Ye et al., 2009).

The WAVE BIOREACTOR™ system, as developed by Singh (Singh, 1999), comprises a pre-sterilized, flexible and disposable culture chamber (CELLBAG™) $CO_2$- and/or $O_2$-air mix controllers, and a pneumatically-controlled platform for rocking and heating the CELLBAG™. The rocking motion generated by this platform provides mixing and gas transfer in the CELLBAG™.

The WAVE BIOREACTOR™ system can be further equipped to provide online pH and dissolved oxygen (DO) monitoring and real-time feedback control (Mikola et al., 2007; Tang et al., 2007). However, the additional devices required, as well as the need for specially-designed bags to accommodate the pH and DO probes, increase the operational cost and complexity of this system. In addition, the base addition required to raise culture pH to the defined setpoint in pH-controlled bioreactors increases the culture osmolality. Depending on the extent of the osmolality increase in the bioreactor, the associated decrease in cell growth and viability (deZengotita et al., 2002; Zhu et al., 2005) may offset the benefits of pH control. In addition, if the pH probe malfunctions, the resulting pH perturbations may alter cell metabolism and promote cell death (Miller et al., 1988; Osman et al., 2002).

Tight pH and DO controls may not be necessary for certain cell culture applications, such as, for example, the routine passage of cells in small-scale culture systems, such as shake flasks and spinners, for cell maintenance and expansion. However, pH and DO extremes are detrimental to cell growth and viability (Lin et al., 1993; Link et al., 2004; Miller et al., 1988; Osman et al., 2001), and may affect product quality (Restelli et al., 2006; Yoon et al., 2005). Therefore, it is critically important to maintain some control over such growth conditions of cells for all stages of biologics manufacturing. Researchers previously demonstrated success in culturing CHO cells in a pH range of 6.8-7.3 and in the DO range of 10-100% of air saturation (Link et al. 2004; Restelli et al. 2006; Trummer et al. 2006; Yoon et al. 2005).

The added features of conventional bioreactors such as real-time pH monitors and DO monitoring control add significantly to the cost and labor-intensity of cell culture in biological manufacturing. Further, the failure or malfunction of these features can cause unacceptable variations and potential loss of the cell culture which is very costly in time and resources.

Thus, there is a need for improved methods for culturing eukaryotic cells without the need for introduction of strong bases, and without additional monitoring and real-time control of pH and DO.

SUMMARY OF THE INVENTION

The invention provides an apparatus and method to maintain pH in a cell culture system without the addition of base. In a bicarbonate-containing cell culture medium, the amount of $CO_2$ in the medium affects the pH of the medium, based on the carbonic acid-bicarbonate buffer equilibrium (Equation 1):

$$CO_2 + HOH \Longleftrightarrow H_2CO_3 \Longleftrightarrow H^+ + HCO_3^-$$

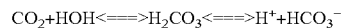

$$pH = pK - \log([CO_2]/[HCO_3^-])$$

Thus, the invention exploits this relationship to adjust the pH of cell culture medium without the need for addition of strong acids or bases by increasing or decreasing the dissolved $CO_2$ concentration using the dynamic interface of a liquid phase and gas phase of a cell culture system. The invention provides a method for achieving this modulation and an apparatus for practicing the method.

In general, the apparatus of the invention is supplied with air, oxygen or a combination of these gases to maintain the dissolved oxygen of the cell culture. By providing a gas mixture (which may be manipulated in terms of its composition and the rate of introduction) to the head space of the apparatus, $CO_2$ can either be added to or removed from the cell culture medium depending on the differential concentration of $CO_2$ between the liquid and gas phase. The removal of $CO_2$ from the head space will increase the culture pH as dissolved $CO_2$ in the medium will diffuse out into the head space. Conversely, when $CO_2$ is added to the apparatus at a concentration that is higher than that of the medium, the $CO_2$ will dissolve into the medium and the culture pH will decrease. This invention provides a method that allows $CO_2$ transfer into and out of the cell culture to maintain culture pH without addition of base.

Thus, the invention provides a method for culturing eukaryotic cells comprising eukaryotic cells in a bicarbonate-containing culture liquid in a vessel, wherein the vessel has walls that encapsulate the cell culture and a gas phase head space above said cell culture. The vessel also comprises at least one port that provides an entrance and an egress of gas from said head space. The vessel is agitated to provide a dynamic interface between the liquid phase and the gas phase. The pH of the culture may be monitored and a gas is provided to the head space through said port wherein the gas contains an amount of $CO_2$ to effect a decrease in the pH as more $CO_2$ dissolves into the cell culture, or accumulated $CO_2$ is removed from the head space through the port to effect an increase in the pH of the cell culture. The pH is thus maintained at a predetermined range.

Generally, the partial pressure of dissolved $CO_2$ in the cell culture medium is maintained at an amount of 1 to 200 mmHg. In some embodiments the partial pressure of dissolved $CO_2$ is 10 to 180 mmHg. In some embodiments the partial pressure of dissolved $CO_2$ is 20 to 150 mmHg. In some embodiments the partial pressure of dissolved $CO_2$ is 100-180 mmHg. In some embodiments the partial pressure of dissolved $CO_2$ is 20 to 80 mmHg. In some embodiments the partial pressure of dissolved $CO_2$ is 30 to 60 mmHg. In some embodiments the partial pressure of dissolved $CO_2$ is 35 to 50 mmHg. In some embodiments the partial pressure of dissolved $CO_2$ is 40 mmHg.

Head space clearance may be performed continuously or intermittently.

In general, the DO is maintained above 10%. In some embodiments, the DO is maintained above 20%. In some embodiments, the DO is maintained above 30%. In some embodiments, the DO is maintained above 40%. In some embodiments, the DO is maintained above 50%. In some embodiments, the DO is maintained above 60%.

In some embodiments, the flow rate of gas into the vessel is 0.001 headspace volume per minute (hvm). In some embodiments, the flow rate of gas into the vessel is 0.005 hvm. In some embodiments, the flow rate of gas into the vessel is 0.01 hvm. In some embodiments, the flow rate of gas into the vessel is 0.02 hvm. In some embodiments, the flow rate of gas into the vessel is 0.05 hvm. In some embodiments, the flow rate of gas into the vessel is 0.1 hvm. In some embodiments, the flow rate of gas into the vessel is 0.2 hvm. In some embodiments, the flow rate of gas into the vessel is 0.5 hvm. In some embodiments, the flow rate of gas into the vessel is 0.9 hvm. In some embodiments, the flow rate of gas into the vessel is 1.0 hvm.

The eukaryotic cells may be vertebrate cells, such as, but not limited to cells from frogs, rabbits, rodents, sheep, goats, dogs, cats, cows, horses, pigs, non-human primates, or humans.

The method may be performed in a vessel that has rigid or pliable walls, such as a plastic container or disposable culture bag.

The vessel may be agitated by any means that provides a dynamic interface between the liquid phase and the gas phase in the vessel. Such agitation may be for example, by rocking, an orbital motion, a figure eight motion, rotational motion, shaking and the like.

In some embodiments, the agitation is performed by rocking. The rocking speed and rocking angle may be adjusted to achieve a desired agitation. In some embodiments the rock angle is 20°, 19°, 18°, 17°, 16°, 15°, 14°, 13°, 12°, 11°, 10°, 9°, 8°, 7°, 6°, 5°, 4°, 3°, 2° or 1°. In certain embodiments, the rock angle is between 6-16°. In other embodiments, the rock angle is between 7-16°. In other embodiments, the rock angle is between 8-12°.

In some embodiments, the rock rate is 1, 2, 3, 4, 5, 6, 7, 8, 9, 10, 11, 1 12, 13, 14 15, 16, 17, 18, 19, 20, 21, 22, 23, 24, 25, 26, 27, 28, 29, 30, 31, 32, 33, 34, 35, 36, 37, 38, 39, 40 rpm. In some embodiments, the rock rate is between 19-25 rpm. In some embodiments, the rock rate is between 20-24 rpm. In some embodiments, the rock rate is between 21-23 rpm.

The method may be performed in which the vessel contains a single port that allows ingress and egress of gas from the head space of the culture. Alternatively, the vessel may contain a plurality of ports.

The pH of the culture is monitored either continuously or intermittently and gas is infused into the head space such that the $CO_2$ level of the gas in the head space is provided either to increase or decrease the concentration of dissolved $CO_2$ in the liquid phase of the culture such that the pH of the liquid phase is adjusted to a predetermined value.

In an alternative embodiment, the method may include a step of perfusing fresh culture medium into the cell culture through a medium port. The fresh medium has a pH that provides adjustment of the overall pH of the cell culture upon addition such that the pH of the fresh medium is partially maintaining the cell culture at a predetermined pH range. The modulation of pH using fresh medium having a predetermined pH is helpful in the culture method, but is not sufficient to completely control the pH.

The method is adaptable for any size culture. In some embodiments, the method is performed in disposable bioreactor bags which are available commercially. Such bioreactor bags are available in such volumes as 500 mL, 1 L, 2 L, 10 L, 20 L, 50 L, 100 L, 200 L, 500 L, and 1000 L.

Various parameters of the culture may be monitored and controlled. Such parameters may be controlled in an automated process as calculations are performed by a computer. Some parameters that may be controlled, alone or in combination, include, but are not limited to, gas flow, pH, dissolved $CO_2$ concentration, temperature, and agitation.

The invention also provides an apparatus for performing the method of the invention.

BRIEF DESCRIPTION OF THE DRAWINGS

FIG. 6 shows the cell culture growth profile and the pH profile for a batch (days 0-6)/perfusion (days 6-14) process. (Panel A) packed cell volume in % PCV; (Panel B) cell viability; (Panel C) pH profile; (Panel D) cell growth in viable cell count (VCC) measured by VICELL™ AS.

DETAILED DESCRIPTION OF THE INVENTION

Figure 1:
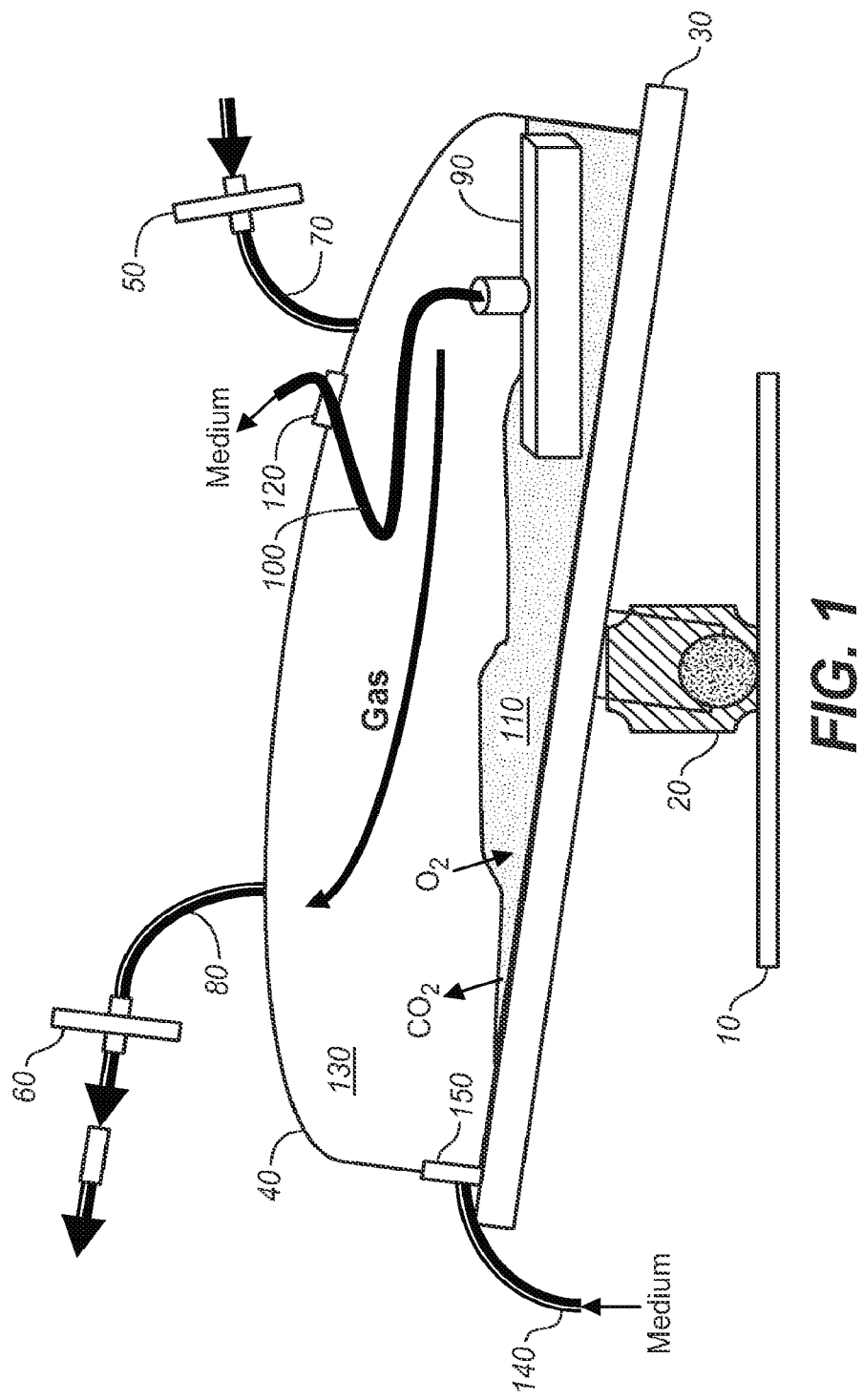
FIG. 1 shows an example of an apparatus of the invention that includes a perfusion filter. The apparatus includes an inlet port and an outlet port for gas, a port to provide fresh medium to the culture, a perfusion filter to remove spent medium a rocking deck and base. The rocking motion allows the agitation to provide efficient transfer of $O_2$ and $CO_2$ in and out of the cell culture medium.

The person of skill in the art is well acquainted with many protocols and methods for culturing eukaryotic cells, and may culture media for the same. Such protocols and culture media are described in the literature and textbooks such as in ANIMAL CELL CULTURE, A PRACTICAL APPROACH 2$^{ND}$ ED., Rickwood, D. and Hames, B. D., eds., Oxford University Press, New York (1992). General use methods are also available on the internet such as at: protocol-online.org/prot/Cell_Biology/Cell_Culture. Cell culture medium is also available commercially from a variety of well-known sources. All literature cited herein is hereby incorporated by reference.

Definitions

The general cell culturing techniques and procedures described or referenced herein are well understood and commonly employed using conventional methodology by those skilled in the art. As appropriate, procedures involving the use of commercially available kits and reagents are generally carried out in accordance with manufacturer defined protocols and/or parameters unless otherwise noted.

Before the present methods are described, it is to be understood that this invention is not limited to the particular methodology, protocols, cell lines, animal species or genera, constructs, and reagents described as such may, of course, vary. It is also to be understood that the terminology used herein is for the purpose of describing particular embodiments only, and is not intended to limit the scope of the present invention which will be limited only by the appended claims.

It must be noted that as used herein and in the appended claims, the singular forms "a," "and," and "the" include plural referents unless the context clearly dictates otherwise. All numbers recited in the specification and associated claims (e.g., 1 to 200 mm Hg, etc.) are understood to be modified by the term "about."

All publications mentioned herein are incorporated herein by reference to disclose and describe the methods and/or materials in connection with which the publications are cited. Publications cited herein are cited for their disclosure prior to the filing date of the present application. Nothing here is to be construed as an admission that the inventors are not entitled to antedate the publications by virtue of an earlier priority date or prior date of invention. Further the actual publication dates may be different from those shown and require independent verification.

As used herein, "about" refers to a value that is 10% more or less than a stated value.

As used herein, "agitate" refers to perturb such that the liquid phase of the culture is in dynamic interaction with the gas phase above the culture. Agitate may refer to a motion such as shaking, stirring, rocking, orbital shaking, rolling, figure-eight shaking or any means to make the liquid phase non-static and increase the diffusion of gases in and out of the liquid phase.

As used herein, "gas" or refers to a pure gas or mixture of gases which may include nitrogen, oxygen, and carbon dioxide. Typically, nitrogen is present in an amount of about 60 to 90% of the total gas concentration, oxygen is present in an amount of about 10 to 40% of the total gas concentration and carbon dioxide is present in an amount of about 0 to 50% of the total gas concentration.

As used herein, "bicarbonate-containing cell culture liquid" refers to a suitable culture medium for culturing eukaryotic cells which contains, as part of its composition, a bicarbonate buffering system. The medium may also contain additional buffering agents such as HEPES or MOPS, or the like, but must contain a bicarbonate based system as well.

As used herein, "cell culture" refers to a liquid preparation containing eukaryotic cells in a liquid medium containing buffering agents and nutrients required for growth and/or maintenance of viable cells.

As used herein, "concentration of dissolved CO$_2$" is expressed by the relative measure partial pressure of CO$_2$ in mmHg. Therefore, partial pressure of dissolved $CO_2$ is used as a reflection of the concentration of dissolved $CO_2$.

"DO" refers to dissolved oxygen.

As used herein, "dynamic interface" refers to an enhanced active exchange of gases between liquid phase and gas phase provided by agitation of the cell culture.

As used herein, "eukaryotic cells" refers to animal cells which may be invertebrate or vertebrate cells.

As used herein, "head space" refers to a gas phase above the liquid phase of the cell culture with the vessel used to culture cells.

As used herein, hvm refers to head space volume per minute and indicates the rate at which the gas in the head space is cleared.

$k_L a$ refers to the volumetric oxygen transfer coefficient.

$k_L a^{CO2}$ refers to the volumetric carbon dioxide transfer coefficient.

LPM refers to liters per minute of gas flow.

As used herein, "modulate" refers to effecting an increase or decrease in a value.

As used herein, "monitor" refers to tracking of a particular value by sampling and analyzing to determine such value either intermittently or continuously.

$pCO_2$ refers to partial pressure of dissolved $CO_2$ concentration.

As used herein, "port" refers to an access point to an otherwise closed system.

As used herein, "predetermined" refers to a value selected in advance for a particular parameter that is used as a goal value.

As used herein "rpm" refers to rocks per minute.

VCC refers to viable cell concentration.

As used herein, "vessel" refers to a container. As used herein such vessel may be, for example, a flask, bioreactor, disposable bioreactor bag, culture chamber, and the like.

As used herein "vvm" refers to vessel volume per minute.

Theoretical Aspects $O_2$ Transfer in WAVE BIOREACTOR™ Culture

To determine the rate of $O_2$ transfer in the WAVE BIOREACTOR™, we assume a sufficiently fast response time for the online DO probe, ideal-mixing in the CELLBAG™, and domination of mass transfer resistance by the liquid-phase interface. Under these assumptions, the following mass balance equation would approximate the rate of $O_2$ transfer from the gas phase to the liquid phase:

$$\frac{dO_2}{dt} = k_L a \cdot (O_2^* - O_2) \qquad (1)$$

where $O_2^*$ is the saturated DO concentration in the medium and $O_2$ is the DO concentration in the medium. Taking $O_2$ to be zero at time zero, the equation would yield:

$$\ln\left(\frac{O_2^*}{O_2^* - O_2}\right) = k_L a \cdot t \qquad (2)$$

By plotting ln $$\left(\frac{O_2^*}{O_2^* - O_2}\right)$$

as a function of time, the slope of the best-fit line would provide the $k_L a$ for the system.

To increase the rate of $O_2$ transfer in the WAVE BIOREACTOR™ (equation 1), we could either increase the $k_L a$ for the system, or increase the concentration gradient ($O_2^*$—$O_2$), or increase both. To increase $k_L a$ for the WAVE BIOREACTOR™ system, we could increase the rock rate, rock angle, or air flow rate (Mikola, 2007; Singh, 1999). To increase the concentration gradient ($O_2^*$—$O_2$) that provides the driving force for the $O_2$ transfer from the gas to the liquid phase, we could increase the percentage of $O_2$ in the inlet gas to increase $O_2^*$.

$CO_2$ Transfer in WAVE BIOREACTOR™ Culture

In a simplified model, gaseous $CO_2$ ($CO_{2(g)}$) in the CELLBAG™ exists in equilibrium with dissolved $CO_2$ ($CO_{2(aq)}$) in the culture medium:

$$CO_{2(g)} \leftrightarrow CO_{2(aq)} \qquad (3)$$

The $CO_{2(aq)}$ in turn exists in equilibrium with carbonic acid ($H_2CO_3$), which can dissociate into bicarbonate ($HCO_3^-$):

$$H_2O + CO_{2(aq)} \leftrightarrow H_2CO_3 \leftrightarrow HCO_3^- + H^+ \qquad (4)$$

Further dissociation of the $HCO_3^-$ into carbonate ($CO_3^{2-}$) should be negligible in the pH 4-8 range (Royce and Thornhill, 1991).

The rate-limiting step for $CO_2$ evolution from the culture medium should be the gas-liquid mass transfer (equation 3). Assuming the $CO_2$ concentration in the liquid at the interface is in equilibrium with that in the bulk gas, the following mass balance equation would approximate the rate of $CO_2$ transfer from the liquid phase to the gas phase:

$$\frac{dCO_{2(aq)}}{dt} = k_L a^{CO_2} \cdot (CO_{2(aq)}^* - CO_{2(g)}) \qquad (5)$$

where $k_L a^{CO_2}$ is the volumetric dissolved carbon dioxide transfer coefficient.

Without a dissolved $CO_2$ probe in the WAVE BIOREACTOR™, we could not make real-time $CO_2$ measurements to directly calculate the rate of $CO_{2(aq)}$ transfer. However, based on our knowledge of the bicarbonate-buffering system in our culture medium, we expect $CO_2$ stripping to increase the culture pH because the equilibria in equations 3 and 4 would shift to the left. Assuming a sufficiently fast response time for the online pH probe, the pH profile it generates in a dynamic $CO_{2(aq)}$ transfer study should provide an indirect estimate of the rate of $CO_{2(aq)}$ stripping.

To increase culture pH, we could increase the rate of $CO_2$ stripping in the WAVE BIOREACTOR™ (equation 5) by either increasing the $k_L a^{CO_2}$ for the system, or by increasing the driving force ($CO_{2(aq)}$—$CO_{2(g)}$) for the $CO_2$ transfer, or by increasing both. Specifically, to increase $k_L a^{CO_2}$ for the WAVE BIOREACTOR™ system, we could increase the rock rate and rock angle. To increase the driving force ($CO_{2(aq)}$—$CO_{2(g)}$), we could decrease the percentage of $CO_2$ in the inlet gas to decrease $CO_{2(g)}$. According to Henry's law, the partial pressure of $CO_{2(g)}$ ($pCO_{2(g)}$) in the CELLBAG™ headspace would limit the $CO_{2(aq)}$ concentration in the medium:

$$CO_{2(aq)} = \frac{pCO_{2(g)}}{H} \qquad (6)$$

where H=Henry's law constant for $CO_2$.

Conversely, to decrease culture pH, we could increase the concentration of $CO_{2(g)}$ in the inlet gas to increase $CO_{2(aq)}$, and thereby shift the equilibria in equation 4 to the right.

Method of the Invention

In the method of the invention, eukaryotic cells are cultured in a suitable culture medium and temperature to permit viability of the cells. As is known to one of skill in the art, different cell types may be grown in different media. The skilled artisan can easily choose which medium is best suited for a particular cell type and/or particular application. In the method of the invention, the medium must contain a bicarbonate buffering system in order to permit modulation of pH by $CO_2$. The medium may contain additional agents that act as a buffer.

The eukaryotic cells that may be used in the method of the invention include animal cells, which may be invertebrate as well as vertebrate cells. Invertebrate cells include insect cells (e.g., *Spodoptera frugiperda, Bombyx mori*, and *Trichoplusia ni* cells). Vertebrate cells include mammalian and non-mammalian cells. Vertebrate cells include, but are not limited to cells from frogs (e.g., *Xenopus laevis*), lagomorphs (e.g., rabbits and hares), rodents (e.g., rats, hamsters, jirds, gerbils, and mice), cats, dogs, sheep, cattle, goats, pigs, horses, non-human primates, and humans.

Cells used in the method of the invention may be recombinant or non-recombinant cells. Recombinant cells may include cells engineered to express particular proteins (such as stably or transiently transfected cells), or cells engineered to produce particular RNAs (e.g., siRNA, ribozymes, and the like).

The cells in the appropriate medium are placed into the culture vessel and gas is infused into the head space. In some embodiments, the head space clearance rate is within a range of about 0.002 to 0.1 hvm. In some embodiments, the head space clearance rate is within a range of about 0.007 to 0.08 hvm. In some embodiments, the head space clearance rate is within a range of about 0.009 to 0.06 hvm. In some embodiments, the head space clearance rate is within a range of about 0.01 to 0.04 hvm. In some embodiments, the head space clearance rate is within a range of about 0.02 to 0.03 hvm. In still other embodiments, the head space clearance rate is within a range of about 0.009 to 0.024 hvm. In further embodiments, the head space clearance rate is within a range of about 0.007 to 0.02 hvm. The "hvm" is the ratio of volumetric flow rate of gas (L/min) to the volume of the headspace (L).

In some embodiments, for example, in a 50 L WAVE BIOREACTOR™ bag, with a culture volume of 20 L and a headspace volume of 30 L, the flow rate of gas into the vessel is 0.1 L/min to 1 L/min. In some embodiments, the flow rate of gas into the bag is 0.2 L/min. In some embodiments, the flow rate is 0.3 L/min. In other embodiments, the flow rate of gas is 0.4 L/min. In still other embodiments, the flow rate of gas is 0.5 L/min. In other embodiments, the flow rate of gas is 0.6 L/min. In other embodiments, the flow rate of gas is 0.7 L/min. In still other embodiments, the flow rate 0.8 L/min. In other embodiments, the flow rate is 0.9 L/min.

In general the cell culture should be maintained within a range of about 6 to 8. In some embodiments, the pH is maintained within a range of about 6.6 to 7.6. In some embodiments, the pH is maintained within a range of about 6.9 to 7.5. In some embodiments, the pH is maintained within a range of about 6.8 to 7.2. In some embodiments, the pH is maintained within a range of about 7.0 to 7.3. While the method of the invention does not require monitoring of pH to maintain a pH that is conducive to growing cells in culture, in some embodiments of the method of the invention, the pH of the culture may be monitored (intermittently or continuously). The measurement may be taken in situ or off line.

In some embodiments of the method of the invention, the DO is maintained above 10%. In other embodiments, the DO is maintained above 20%. In other embodiments, the DO is maintained above 30%. In other embodiments, the DO is maintained above 40%. In other embodiments, the DO is maintained above 50%. In other embodiments, the DO is maintained above 60%. In other embodiments, the DO is maintained above 70%. In other embodiments, the DO is maintained above 80%. In other embodiments, the DO is maintained above 90%.

Monitoring of $CO_2$ concentration in liquid medium is well-known in the art and may be accomplished using commercially available technology. The measurement may be taken in situ or off line.

In a particular illustrative embodiment of the method of the invention, a batch process is used wherein cells are cultured with a stepwise fashion. In this method a WAVE BIOREACTOR™ system 50 L bag is used with a 20 L working volume of culture wherein the headspace is infused with gas supplemented with 8% $CO_2$ (v/v) of gas during the first day, 5% $CO_2$ (v/v) of gas the second day and 2% $CO_2$ (v/v) of gas thereafter. The WAVE BIOREACTOR™ is rocked at 21 rpm at 10°, and 0.2 L/min for the inoculation, and then 23 rpm, 10° rock angle and 0.2 L/min for the scale up stage. In this arrangement, it is not necessary to monitor the pH as the pH will be maintained by the parameters used.

In a particular illustrative embodiment of the method of the invention, a perfusion process is used. In this method, a WAVE BIOREACTOR™ 50 L bag is used with a 20 L working volume of culture. The bag is infused with gas that is supplemented with 30% $O_2$ (v/v) two days after the initiation of perfusion. The gas flow rate is increased stepwise from 0.2 L/min on day 0, then increased to 0.4 L/min on day 3, then increased again to 0.6 L/min on day 6. In this arrangement, it is not necessary to monitor the pH as the pH will be maintained by the parameters used.

In another particular illustrative embodiment of the method of the invention, a perfusion process is used. In this method, a WAVE BIOREACTOR™ 50 L bag is used with a 20 L working volume of culture. The bag is infused with gas that is supplemented with 30% $O_2$ (v/v) two days after the initiation of perfusion. The gas flow rate is kept at a constant flow rate of 0.6 L/min. In this arrangement, it is not necessary to monitor the pH as the pH will be maintained by the parameters used.

In yet another particular illustrative embodiment of the method of the invention, a perfusion process is used. In this method, a WAVE BIOREACTOR™ 50 L bag with a 20 L working volume of culture is used. The bag is infused with gas that is supplemented with 30% $O_2$ (v/v) two days after the initiation of perfusion. The gas flow rate is kept at a constant flow rate of 1.0 L/min. In this arrangement, it is not necessary to monitor the pH as the pH will be maintained by the parameters used.

It will be apparent to one of skill in the art that the parameters of the culture conditions (gas concentrations, flow rates, hvm, rock rate, rock angles, etc., may be adjusted using the teachings herein to achieve a pH with the desired range.

Apparatus

The vessel to hold the cell culture medium is not limited to any particular size. The vessel of the invention may be adapted to the size of commonly used bioreactors and disposable culture bags as used in the art, and may be adapted for larger or smaller cultures.

The vessel is not limited to the material used to create the vessel. The vessel may be made from a solid material such as glass or a hard plastic, or may be made of a pliable material such as a soft plastic such as that used to produce disposable bioreactor bags.

The vessel may optionally contain baffles to increase the turbulence of the medium when agitated.

The vessel may be equipped with one or more ports to allow addition or removal of gas and liquids. Gas may be charged into the head space and removed from the head space through one or more ports. In one embodiment, there is a single port that allows both ingress and egress of gas. In other embodiments, there are two ports: one for ingress of gas and one for egress of gas. In other embodiments a plurality of ports are used to allow ingress and egress of gas.

In some embodiments, the apparatus may also comprise a pH monitor that continuously or intermittently monitors the pH of the cell culture medium. The pH monitor may be used in communication with an automated system to gas or degas the head space of the vessel to alter the concentration of $CO_2$ and thereby adjust the pH of the cell culture medium.

In some embodiments, the apparatus of the invention comprises a monitor for $CO_2$ that continuously or intermittently monitors the partial pressure of dissolved $CO_2$ as an indication of the concentration of $CO_2$ in the medium. The $CO_2$ monitor may be used in communication with an automated system to gas or degas the head space of the vessel to alter the concentration of dissolved $CO_2$ such that the actual concentration of $CO_2$ as measured by the $CO_2$ monitor is modulated to adjust the concentration to a predetermined value.

In some embodiments, the apparatus of the invention comprises a monitor for temperature that continuously or intermittently monitors the temperature of the cell culture medium. The temperature monitor may be used in communication with an automated system to increase or decrease the temperature such that the actual temperature as measured by the monitor is modulated to adjust to a predetermined value.

The various parameter monitors may be used alone or in combination and may be controlled using an automated system controlled by a computer. The computer may be programmed to perform the calculations necessary to determine the amount of $CO_2$ to be infused with the gas or degassed from the head space in order to adjust the pH of the cell culture medium. The computer may also perform calculations with respect to temperature, rate of agitation, perfusion of medium and other parameters as well as control the means to adjust the parameters in an automated fashion.

Optionally, apparatus of the invention includes an agitator to agitate the vessel such that the cell culture medium is not static but is in dynamic interface with the gas of the head space. The agitation facilitates diffusion of gas in and out of the cell culture medium. The agitator may be any form known in the art, but includes such non-limiting examples of shakers, orbital shakers, rotators, figure-eight shakers, rocking platforms, rotational platforms, and the like.

The automated gas delivery and gas purging system may include a valve and pump system to deliver pressurized gas through sterile filters with a control gauge for controlling the rate of gas flow into the vessel. Any means known in the art for delivering gas and removing gas may be employed. The gas may be introduced in response to a signal calculated on a computer when the concentration of dissolved $CO_2$ in the cell culture medium deviates from a predetermined value. If the measured concentration of $CO_2$ deviates from the predetermined value, the automated system calculates the amount of $CO_2$ needed to be added to the system or removed from the system, and the gas with the proper amount of $CO_2$ is introduced into the headspace as the resident gas is purged out through the egress port. The computer may perform calculations involving Equations 1, 2 and/or 3 as defined herein and other calculations for regulating the system as will be known to one of skill in the art based on the available literature, commercially available systems and the teachings herein.

Alternatively, or in conjunction with a response system using a monitored concentration of $CO_2$, the automated system may also measure the pH of the culture medium and respond when the measured pH deviates from a predetermined pH for culturing the cells. The automated system may respond to a deviation in $CO_2$ concentration and/or pH and introduce an appropriate amount of $CO_2$ with gas while resident gas is purged out so to appropriately modulate the pH of the culture medium.

The apparatus and method will now be described in a non-limiting example with reference to FIG. 1. Culture vessel (40) contains cell culture medium and cells (110) and head space (130). A gas ingress port (70) with filter (50) is connected to the vessel (40) to allow infusion of gas into head space (130). A gas egress port (80) with filter (60) is connected to vessel (40) to allow egress of gas out of head space (130). Vessel rests on platform (30) which is connected to rocker (20) and base (10) to allow a rocking motion and agitation of cell culture medium (110). Agitation and gas flow within head space (130) allows diffusion of $O_2$ and $CO_2$ in an out of cell culture medium (110). The optional perfusion filter (90) for retaining cells in the culture vessel is connected via tubing (100) to a medium port (120) to allow removal of spent culture medium from the cell culture as necessary.

Cells are cultured in cell culture medium (110) in a vessel (40). The head space (130) in the vessel (40) is filled with gas. The flow of gas through gas ingress port (70) and out gas egress port (80) allows of gas to flow through head space (130) and flow out $CO_2$ that diffuses out of the cell culture medium (110) into head space (130) as the culture is agitated by the rocking motion of the platform (30) on rocker (20) attached to base (10). The reduction of dissolved $CO_2$ in cell culture medium (110) causes an increase in the pH of the cell culture medium (110).

Cells culture medium (110) may be optionally supplement with fresh medium supplied through the medium tubing (140) through the medium port (150) and removed through the perfusion filter (90) up through the medium tubing (100) and out through the medium exit port (120). In this optional feature of the method of the invention, fresh medium is supplied as the original cell culture medium is depleted of nutrients and as cell waste products accumulate and pH decreases. The fresh medium is supplied with a predetermined pH that is sufficient to cause an increase in the pH of the total cell culture medium upon mixing to bring the cell culture medium to a predetermined optimal pH range.

EXAMPLES

A. Principles

Since most mammalian cell culture systems utilize a bicarbonate-containing cell culture medium, the pH control in mammalian cell culture is predominantly performed by base/$CO_2$ additions. The pH control takes advantage of the carbonic acid-bicarbonate buffer system. It has been discovered that in such a system, for example a disposable bag bioreactor, the pH of the culture can be modulated by manipulating the concentration of dissolved $CO_2$ in the medium, which can be modulated by modulating the head space concentration of $CO_2$. Bi-directional pH adjustment is shown possible in the examples herein by modulating the $CO_2$ concentration in the head space. This method will eliminate the use of base to increase pH in a cell culture bioreactor system. If the pH of the cell culture in the disposable bioreactor needs to be decreased, the concentration of $CO_2$ in the head space can be increased by supplementing the incoming gas with $CO_2$. This will enable the $CO_2$ to be transferred into the cell culture. If the pH of the cell culture in the disposable bag needs to be increased, the $CO_2$ concentration in the head space can be decreased or the rate of head space clearance can be increased to facilitate removal of $CO_2$ from the cell culture.

This method of pH maintenance can be extended to a bioreactor system in which the gas transfer in the bioreactor is facilitated mainly by the large surface area created in the bioreactor.

$CO_2$ Addition/Removal Based pH Maintenance Strategy in a Cell Banking Process:

During the initial stages of cell culture, when there is a relatively smaller number of cells, the pH of the cell culture typically rises. To control the pH, $CO_2$ is typically added to the bioreactor to reduce the pH. Normally this addition is accomplished by sparging the $CO_2$ gas through the cell culture in a normal stirred-tank bioreactor. In a disposable bioreactor of the invention, the $CO_2$ concentration in the head space is altered so that the direction of $CO_2$ transfer is from the gas phase to the liquid phase. As the cell concentration increases over the course of the culture, the $CO_2$ concentration in the cell culture also increases and hence the pH typically decreases. In a normal stirred-tank bioreactor with the normal pH feed-back control, base will be added to control the pH. Addition of base increases the pH of the cell culture. In the disposable bioreactor of the invention, the increase in pH can be accomplished by reversing the direction of $CO_2$ transfer by decreasing the concentration of $CO_2$ in the head space as well as increasing the rate of clearance of head space. This method of maintaining the pH of the cell culture by managing the $CO_2$ concentration in the media allows the elimination of using base. Based on the requirement (either increase or decrease the pH) the $CO_2$ concentration in the head space can be decreased or increased, respectively.

A disposable bioreactor system may be used as the bioreactor system to generate high cell density cell banks, such as, but not limited to Master Cell Banks (MCB) and Working Cell Banks (WCB). A perfusion cell culture process is considered to enable production of high cell density cell banks in the disposable bioreactor. The $CO_2$ addition/removal approach is proposed for pH maintenance while developing the cell culture process for generating MCBs and WCBs. In addition to the gas transfer approach to maintain pH, the perfusion of the cell culture allows extra opportunities to maintain pH. In a perfusion cell culture process, fresh cell culture media is continuously added to the bioreactor while the spent culture medium is continuously removed. Perfusion allows for the removal of cell culture by-products that could potentially affect the pH of the cell culture. In addition to the removal of cell culture by-products, the incoming fresh cell culture media pH can also alter the pH of the cell culture. If one knows that the pH of the cell culture is going to decrease, the pH of the incoming media can be increased to compensate for the decrease in pH. Alternatively, the rate of perfusion can also be altered to manage the culture pH. All the above approaches have an impact on pH, but the most important factor that will affect the pH is the $CO_2$ transfer method. The $CO_2$ transfer is also a more reliable approach as gas flow rate and $CO_2$ supplementation in a disposable bioreactor can be controlled effectively without many problems.

During our initial attempts to culture CHO cells in the WAVE BIOREACTOR™ without pH and DO feedback controls, we identified several challenges (FIG. 5): (1) slow growth during the batch culture stage (days 0-6) at approximately 0.3 day$^{-1}$; (2) progressively slower growth during the perfusion culture stage (day 6 onwards), declining from approximately 0.5 day$^{-1}$ during the first 3 days to less than 0.3 day$^{-1}$ thereafter; (3) initial culture pH sometimes exceeded 7.3, and subsequent culture pH frequently dropped below pH 6.8; and (4) DO levels were often below 20% of air saturation after the onset of perfusion on day 6. We encountered the same challenges using CHO cell lines producing other MAbs (data not shown). We attributed the slow growth in batch culture to the high initial pH, and the growth rate decline in perfusion culture to decreasing pH and DO.

In the absence of pH feedback control in the WAVE BIOREACTOR™, the pH in these bicarbonate-buffered cultures should depend on the $CO_2$ content in the headspace of the CELLBAG™. Despite the presence of bicarbonate and HEPES buffers in the medium, culture pH should eventually drop with time as a result of lactate accumulation. To maintain culture pH in our desired 6.8-7.2 range, our strategy was to manipulate $CO_2$ concentration in the CELLBAG™. We would increase $CO_2$ transfer into the medium to decrease the pH during the early stages of batch culture. Conversely, we would strip $CO_2$ from the medium to increase the pH during the later stages of batch or perfusion culture. In the absence of DO feedback control in the WAVE BIOREACTOR™, DO levels should drop with increasing cell densities. To maintain DO>20% of air saturation, we would increase $O_2$ transfer into the cultures by increasing the volumetric oxygen transfer coefficient ($k_La$) for the WAVE BIOREACTOR™ system, and by supplementing the inlet gas with $O_2$.

B. Materials and Methods

1. CHO Cell Lines and Culture Medium

All cell lines used in the Examples were derived from a CHO dihydrofolate reductase-deficient (DHFR-) host adapted to grow in serum-free suspension culture. Each cell line producing a specific monoclonal antibody (MAb) was generated by transfecting the DHFR-host with a DNA plasmid encoding genes for DHFR, MAb light chain (LC), and MAb heavy chain (HC). The stably-transfected cells were subsequently maintained by passaging every 2-5 days in proprietary chemically-defined selective media containing methotrexate. The same medium—containing 1.0 g/L Pluronic F-68, 2.44 g/L sodium bicarbonate, and 15 mM HEPES, in addition to a proprietary blend of nutrients—was used for culturing cells in the WAVE BIOREACTOR™ in both batch and perfusion modes.

2. WAVE BIOREACTOR™ System

The WAVE BIOREACTOR™ system (GE Healthcare, Piscataway, N.J., USA)—used for culturing the CHO cells in batch or perfusion mode—consisted of a rocking platform, a controller unit, and a pre-sterilized, flexible, and disposable bag with inlet and outlet gas filters and multiple sampling ports (Singh, 1999; Tang et al., 2007). Each system was equipped with a heating pad and a gas-mix box to provide temperature control and the required inlet gas composition ($O_2$ and/or $CO_2$ mixed with air), respectively. All cell culture experiments were conducted using a 50-L CELLBAG™ at a working volume of 6 or 20 L, a temperature setpoint of 37° C., a rock rate of 19-25 rpm, and a rock angle of 8-12°. Online pH or DO probes were not installed in the WAVE BIOREACTOR™; instead, different gas-mix and gas flow rate strategies were tested for their ability to maintain culture pH and DO levels within the target range.

3. Batch Culture in WAVE BIOREACTOR™

Batch culture was initiated at 6 L in the WAVE BIOREACTOR™ by inoculating either a regular or a perfusion CELLBAG™ at ~7.5×10$^5$ cells/mL. A few days post-inoculation, when the culture accumulated sufficient cell mass, fresh medium was added to increase the working volume to 20 L. For each passage, the culture was maintained for 2-5 days in batch mode.

4. Perfusion Culture in WAVE BIOREACTOR™

Unless stated otherwise, perfusion culture was initiated after the batch culture accumulated sufficient cell mass at 20-L working volume in a perfusion CELLBAG™ with a rock rate of 23 rpm and a rock angle of 10°, and a perfusion rate of 1 working volume per day. The cell retention device in the perfusion CELLBAG™ consisted of a filter that floated on the liquid surface during the culture process (Tang et al., 2007). The perfusion filter retained the cells in the CELLBAG™ while both fresh medium was added and filtrate was removed continuously. Constant volume was maintained in the perfusion WAVE BIOREACTOR™ by matching the fresh medium addition rate to the filtrate removal rate of one working volume per day.

5. Stirred-Tank Bioreactor Cultures

To compare performance between cultures in a WAVE BIOREACTOR™ and a stirred-tank bioreactor, cells from the same seed train source were inoculated into both a WAVE Bioreactor™ bioreactor and a 20-L stainless steel stirred-tank bioreactor (Applikon, Foster City, Calif., USA) at ~7.5×10$^5$ cells/mL. Cells were first cultured in batch mode and then perfusion was initiated upon accumulation of sufficient cell mass. The working volume was 7 L in batch mode and 15 L in perfusion mode in the stirred-tank bioreactor. Culture temperature, DO, and agitation were maintained at setpoints of 37° C., 30% of air saturation, and 125 rpm, respectively. Culture pH was maintained at 7.15, with a deadband of 0.03, by either addition of 1M sodium carbonate to increase the pH or sparging of $CO_2$ gas to decrease the pH. During perfusion operation, the Centritech centrifuge system (Centritech AB, Norsborg, Sweden) was used to separate cells from the growth medium; cells were retained by the centrifuge and returned to the bioreactor while the supernatant was removed (Johnson et al., 1996). Constant volume was maintained in the bioreactor by matching the fresh medium addition rate to the supernatant removal rate of one working volume per day.

6. Off-Line Sample Analyses

Cultures were sampled and analyzed for viable cell concentration (VCC) and viability (Vi-Cell AS, Beckman Coulter, Fullerton, Calif., USA), as well as for pH, DO, $pCO_2$, glucose, and lactate (Bioprofile 400, Nova Biomedical, Waltham, Mass., USA).

Example 1: Cell-Free Studies: Gas Transfer Measurements

Gas transfer characteristics in the CELLBAG™ affect culture performance because of their effects on DO and pH levels. As the first step towards maintaining pH and DO within our desired ranges, cell-free studies in the CELLBAG™ to measure $O_2$ and $CO_2$ transfer were conducted.

A. $O_2$ Transfer Studies $O_2$ transfer in the 50-L CELLBAG™ was characterized using a simulated culture medium by calculating the volumetric $O_2$ transfer coefficient ($k_L a$) at various combinations of rock rates (20, 30, and 40 rpm), rock angles (8°, 10°, and 12°), and gas flow rates (0.1, 0.2, and 0.3 L/min). The classic dynamic gassing-out method was used to calculate the $k_L a$ (Dunn and Einsele, 1975). The test medium used for these studies was designed to simulate the proprietary cell culture medium: it was composed of 1.0 g/L Pluronic F-68, 2.44 g/L sodium bicarbonate, and 15 mM HEPES. An OxyProbe® DO probe connected to a Model 40 transmitter from the same manufacturer (Broadley-James Corporation, Irvine, Calif., USA) was used to provide online DO measurements.

In preparation for the $O_2$ transfer testing, after a 50-L CELLBAG™ was filled with 25 L of simulated medium, nitrogen ($N_2$) was passed through the gas inlet port. The bag was rocked to facilitate transfer of $N_2$ into the mock medium. The flow of $N_2$ into the headspace was stopped when DO content of the mock medium dropped below 10% of air saturation. Following this de-oxygenation process, the bag was pressed to vent residual $N_2$ from the headspace. Compressed gas was then added to the headspace in the bag while minimizing disturbance to the liquid-gas interface. As soon as the bag was fully inflated, $O_2$ transfer testing was initiated at the defined test conditions for rock rate, rock angle, and gas flow rate. The resulting increase in DO concentration was recorded and was used to determine the $k_L a$ of the system. In addition, off-line DO was measured every minute for the first five minutes, and every five minutes thereafter to verify the accuracy of the online DO readings.

At a constant air flow rate, increasing the rock rate or rock angle increased $k_L a$ (FIG. 2A), presumably by increasing the surface area for oxygen transfer. The $k_L a$ numbers we obtained at the lowest rock rate tested (20 rpm) are comparable to what other researchers reported for the WAVE BIOREACTOR™ system (Mikola et al., 2007; Singh, 1999). These $k_L a$ numbers are also comparable to those obtained for our in-house stirred tank bioreactors (data not shown).

Figure 2:
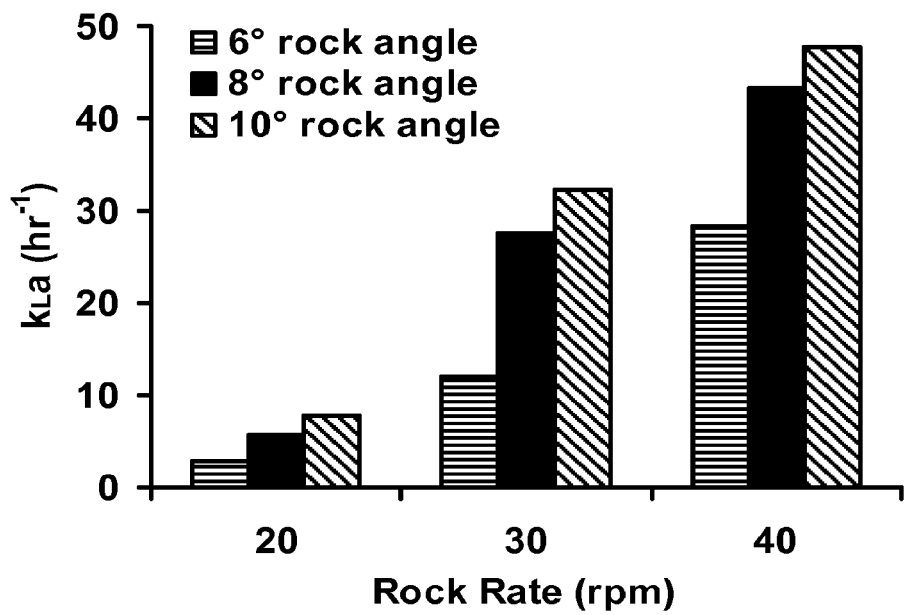
FIG. 2 shows cell-free studies to measure oxygen transfer in the WAVE BIOREACTOR™. (Panel A) Effect of rock rate and rock angle on $k_La$ at constant air flow rate of 0.2 L/min; (Panel B) Effect of rock rate, rock angle, and air flow rate on $k_La$; (Panel C) raw DO data for different rock angle, rock rate and a constant gas flow rate of 0.2 L/min (also referred to herein as LPM); (Panel D) raw DO time-course data for two different rocking set points with different gas flow rates.
Figure 2:
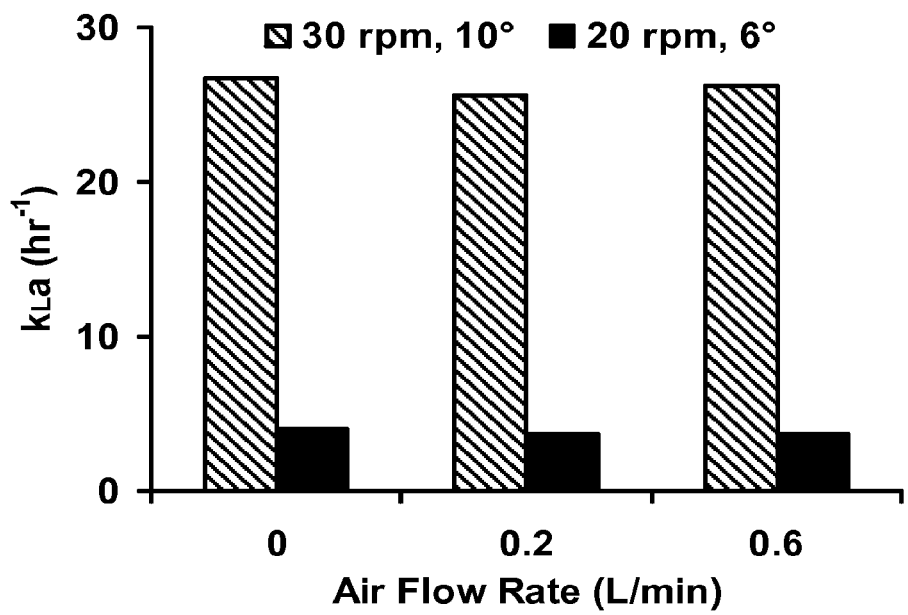
Figure 2:
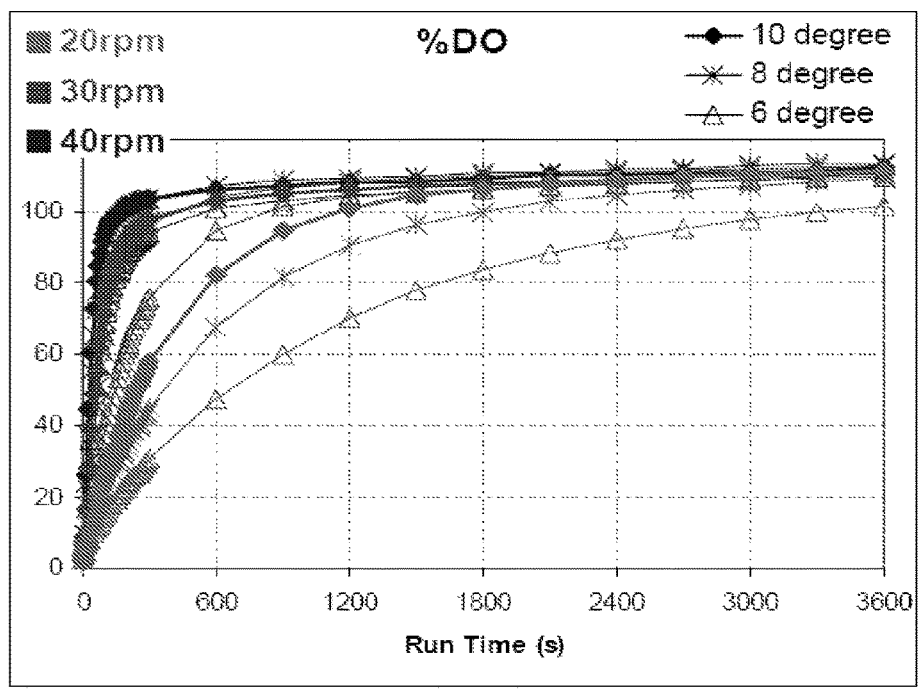
Figure 2:
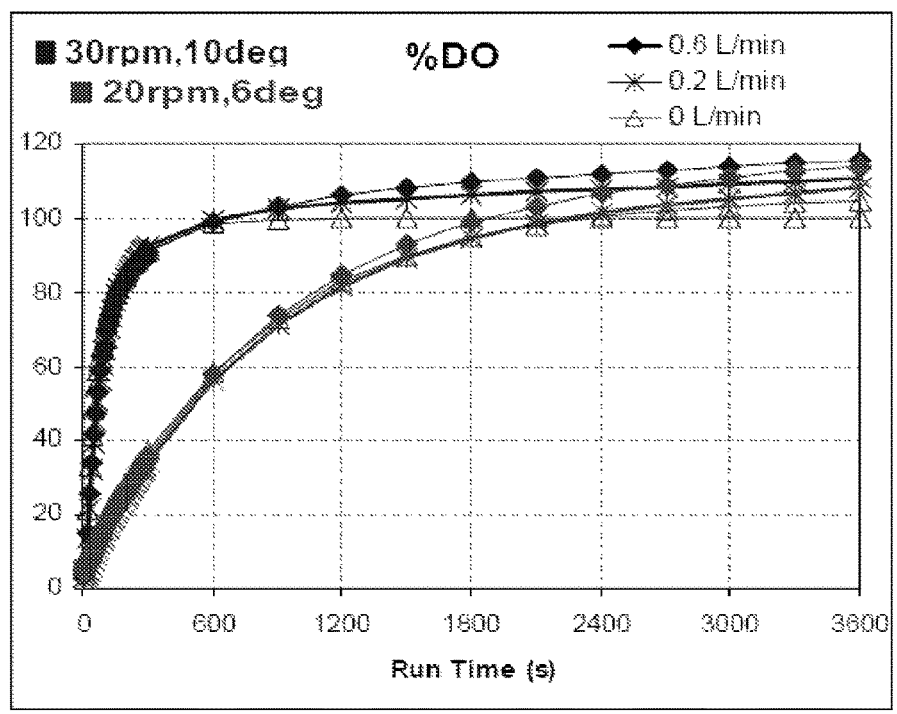

In an $O_2$ transfer study of the WAVE BIOREACTOR™ system at a constant rock rate of 20 rpm, increasing the air flow rate from 0.01 vvm to 0.05 vvm increased $k_L a$ from ~2 $h^{-1}$ to ~3 $h^{-1}$ at the 2-L scale, and increasing the air flow rate from 0.01 vvm to 0.1 vvm increased $k_L a$ from ~0.5 $h^{-1}$ to ~3 $h^{-1}$ at the 20-L scale, (Singh, 1999). By contrast, in our study at the 50-L scale, increasing the air flow rate from 0 vvm to 0.02 vvm at two different combinations of rock rate and rock angle did not increase $k_L a$ (FIG. 2B). The maximum air flow rates we used may have been too low to affect liquid mobility at the gas-liquid interface to have any significant effect on $k_L a$.

The oxygen transfer capacity of the 50 L disposable bag was evaluated by determining the mass transfer coefficient, $k_L a$. FIG. 2C shows the DO concentration over time for a constant gas flow rate and FIG. 2D shows the effect of gas flow rate on dissolved oxygen. For aggressive rocking conditions (higher rock rate and rock angle) the mass transfer coefficient is high. Surprisingly, head space clearance rate, however, does not have an effect on $k_L a$ with respect to oxygen transfer. The simulated medium was de-oxygenated before the start of the experiment. The concentration of oxygen in the gas was higher than the concentration of oxygen in the simulated medium. Hence, oxygen was transferred from the gas phase to the liquid phase. With aggressive rocking conditions, the gas-liquid interface increases because of more wave formations (this is referred to herein as having a dynamic interface). This increase in surface area appears to cause the high rate of oxygen transfer. When the gas flow rate is increased or decreased, the head space clearance rate is changed accordingly. The change in head space clearance does not change the differential concentration of oxygen between the gas and the liquid phase. Hence there gas flow rate appears to have no effect on mass transfer coefficient for oxygen. When the concentration of oxygen in the simulated medium equals that of the head space, the oxygen transfer will stop.

B. $CO_2$ Transfer Studies

After the simulated medium was de-oxygenated by the method used for the $O_2$ transfer studies, $CO_2$ was supplied to the CELLBAG™ through the same inlet port used to supply $N_2$. Supply of $CO_2$ was stopped when the online pH probe read 7.0, and the headspace was cleared using the same method described in the $O_2$ transfer studies. When the bag was fully inflated, $CO_2$ transfer testing was initiated at the defined test conditions for rock rate, rock angle, and gas flow rate. The resulting increase in pH was recorded with a disposable online pH probe connected to a pH20 transmitter provided by the same manufacturer (GE Healthcare, Piscataway, N.J., USA). The pH increased because $CO_2$ was stripped from the bicarbonate-based simulated medium. To verify the accuracy of the online pH readings, off-line pH in the simulated medium was measured every minute for the first five minutes, and every five minutes thereafter. By plotting the online pH measurements against time, the slope of the best-fit line provided the rate of pH change and thereby indicated the rate of $CO_2$ transfer from the simulated medium to the headspace in the CELLBAG™.

Although other researchers have characterized $O_2$ transfer in the WAVE BIOREACTOR™ (Mikola et al., 2007; Singh, 1999), we have not found reports on $CO_2$ transfer in cell culture systems with Wave-induced agitation. To characterize $CO_2$ transfer in the WAVE BIOREACTOR™, we used simulated medium containing sodium bicarbonate at the same concentration (2.44 g/L) as in our cell culture medium. In this bicarbonate-buffered cell-free system, $CO_2$ removal from the liquid phase would increase the pH of the system in the absence of active pH control. Instead of relying on $CO_2$ probes for direct $CO_2$ measurements in the simulated medium, we used the pH profile from an online pH probe in the WAVE BIOREACTOR™ to assess the relative rate of $CO_2$ stripping.

In this study, the pH profile in the WAVE BIOREACTOR™ separated into two phases (FIGS. 3A and 3B). In the first phase, pH increased rapidly between 0 to 5 minutes at ~1-4 pH units per hour. In the second phase, pH increased more gradually from 5 to 60 minutes at <0.5 pH units per hour. During this second phase (5-60 minutes), different rock rates and rock angles had negligible impact on the rate of pH increase: at the constant air flow rate of 0.2 L/min, the pH increased at 0.2 units per hour, irrespective of the rocking condition (FIG. 3A). By contrast, higher air flow rates increased the rate of pH change during this second phase (5-60 minutes): when air flow rate increased from 0 L/min to 0.6 L/min, the rate of pH change increased from 0-0.1 units per hour to 0.4 units per hour (FIG. 3B). In the absence of air flow (0 L/min), the minimal pH increase (≤0.1 units per hour) observed during the second phase (5-60 minutes) suggests that $CO_2$ exchange between the simulated medium and the headspace in the CELLBAG™ approached an equilibrium in approximately 5 minutes. To achieve additional pH increase beyond the first 5 minutes, the driving force for $CO_2$ stripping could be augmented by increasing the air flow rate to increase the rate of headspace clearance and thereby minimize the $CO_2$ concentration in the headspace.

FIG. 3C shows the calculated rate of change of pH for data from FIG. 3A. FIG. 3D shows the calculated rate of change of pH for data from FIG. 3B. The bi-phasic behavior may explained by the high gas transfer rates created by both the high surface area of the waves and the continuous sweeping of head space by the incoming gas. The high surface area facilitates fast $CO_2$ transfer from the liquid phase to the gas phase. The fast transfer is a result of the differential concentration of $CO_2$ between the gas and the liquid phase. This difference in concentration was at the highest during the start of the experiment and this difference was reduced continuously as more $CO_2$ was transferred from the liquid phase to the gas phase. As the differential concentration of $CO_2$ between the gas and the liquid phase was reduced, the rate of change in pH was also reduced. In FIG. 3A, the rate of change in pH was very high for the first phase (0-5 minutes) compared to the second phase (5-60 minutes). The gas flow rate was kept the same for cases shown in FIG. 3A. After the initial transfer of $CO_2$, the rate of $CO_2$ transfer depends on the $CO_2$ concentration in the head space. For the same head space clearance rate, the rate of change in pH after the initial 5 minutes was the same irrespective of the rocking conditions. The calculated value for the rate of change in pH is shown in FIG. 3C.

When the gas flow rate was changed, the rate of clearance of the head space was also changed. The data for rise of pH for different gas flow rates is shown in FIG. 3B. Bi-phasic behavior was observed for these cases also. However, between the cases with the same gas flow rate and the cases where the gas flow rate was varied, the difference is that the rate of pH change of the second phase (5-60 minutes) varied depending on the gas flow rate compared to being similar for cases with the same gas flow rate. Since changing the gas flow rate changes the rate of head space clearance, the $CO_2$ in the head space was removed at different rates.

The initial fast gas transfer is the result of the disposable bag's property to create large surface area. This initial gas transfer depends mainly on the rocking conditions (rock rate and rock angle). However, the sustained removal of $CO_2$ from the medium depends on the head space $CO_2$ concentration. The rate of head space clearance depends on the gas flow rate.

Example 2: Cell Growth Characteristic Studies

A. Batch Cultures
1. Initial Experiment
Cell Culture Medium:
A serum-free cell culture medium was used to grow Chinese Hamster Ovary (CHO) cells. The cell culture medium was derived from a 1:1 mixture of DMEM and Ham's F-12 based media by modifying some of the components such as amino acids, salts, sugar and vitamins. This medium lacks glycine, hypoxanthine, and thymidine. This medium consisted of 15 mM HEPES (4-(2-hydroxyethyl)-1-piperazineethanesulfonic acid) and 2.44 g/L of sodium bicarbonate. The concentration of these salts may be modified. The medium was supplemented with trace elements, recombinant human insulin, and a cell protective agent, Lutrol F-68 Prill (an equivalent may be used).

Mammalian Cell Cultivation:
Transfected Chinese Hamster Ovary (CHO) cells were grown from a 1 mL or 10 mL vial bank stored in liquid nitrogen. The selected frozen vial was thawed into a culture medium containing sodium bicarbonate in either a spinner flask, a shake flask or a stirred-tank bioreactor. The cells were passaged every 2-7 days. This culture was referred to as the "seed train." Cells from the seed train were transferred to the disposable bag to initiate cell culture in the disposable bag.

Analysis:

A blood gas analyzer (NOVA BIOPROFILE® 400) was used for off-line analysis. Cell culture pH, partial pressure of dissolved oxygen and $CO_2$, concentration of glucose, lactate and ammonia were measured using this offline analyzer. Cell viability and viable cell concentration (VCC) measurements were made using Beckman-Coulter's VICELL™ AS or VICELL™ XR. In addition to the cell concentration measurements, the amount of biomass was also measured by recording the percent packed cell volume (% PCV).

Example 3: Detailed Analysis Using Several CHO Cell Lines

A. Batch Process:

By decreasing the $CO_2$ concentration in the gas supplied to the CELLBAG™ over the course of batch culture, we should be able to lower the initial high pH (>7.3) and minimize the subsequent pH decrease in the WAVE BIOREACTOR™ system. After testing different $CO_2$ gas overlay strategies in WAVE BIOREACTOR™ batch cultures using several CHO cell lines (data not shown), we defined a "8-5-2" stepwise strategy for both the inoculation and scale-up stages: the air pumped into the CELLBAG™ was supplemented with $CO_2$ gas at 8% (v/v) during the first day, at 5% (v/v) during the second day, and at 2% (v/v) thereafter.

Based on the results from cell-free studies, we selected the following rock rate, rock angle and air flow rate as the process setpoints for our WAVE BIOREACTOR™ batch cultures: 21 rpm, 10° rock angle, and 0.2 L/min for the inoculation; 23 rpm, 10° rock angle, and 0.2 L/min for the scale-up stage. To test reliability of these process setpoints, we designed a full-factorial experiment (Table 1). When the process conditions deviated from the center points, we observed negligible effect on cell growth and $pCO_2$ profiles, and culture pH remained within 6.8-7.2 and DO>50% for both cell lines tested (FIG. 4).

TABLE 1

Figure 4:
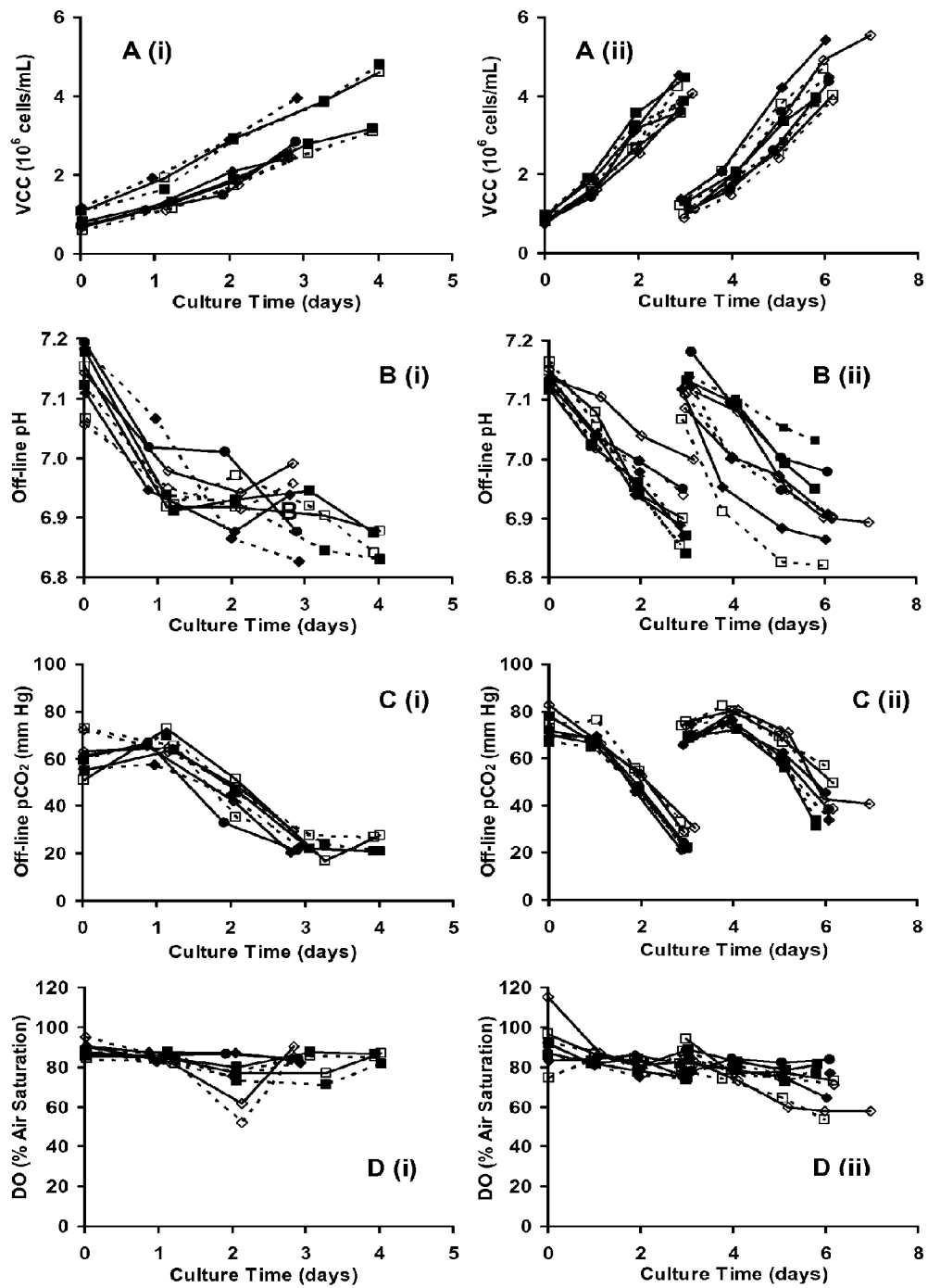
FIG. 4 shows (Panel A) VCC, (Panel B) off-line pH, (Panel C) off-line $pCO_2$, and (Panel D) off-line DO profiles for WAVE BIOREACTOR™ batch cultures. Process conditions are summarized in Table 2, below. Only the inoculation stage was evaluated for (i) cell line producing MAb B, whereas both the inoculation and scale-up stages (during which working volume increased from 6 L to 20 L) were evaluated for (ii) cell line producing MAb C. During each stage, the air pumped into the headspace was supplemented with CO$_2$ at 8% (v/v) during the first day, at 5% (v/v) during the second day, and at 2% (v/v) thereafter.

Conditions tested in WAVE BIOREACTOR™ batch cultures for cell lines producing MAb B and MAb C (FIG. 4). Full-factorial experiment was designed around three process parameters-in rock rate, rock angle, and air flow rate into headspace-for both the inoculation and scale-up stages in batch culture.

| | Inoculation | | | | Scale-up | | |
|---|---|---|---|---|---|---|---|
| Symbol | Rock Rate (rpm) | Rock Angle (°) | Air Flow Rate into Headspace (L/min) | Symbol | Rock Rate (rpm) | Rock Angle (°) | Air Flow Rate into Headspace (L/min) |
| -□- | 19 | 8 | 0.1 | -□- | 21 | 8 | 0.1 |
| -◇- | 19 | 12 | 0.1 | -◇- | 21 | 12 | 0.1 |
| -■- | 19 | 8 | 0.3 | -■- | 21 | 8 | 0.3 |
| -◆- | 19 | 12 | 0.3 | -◆- | 21 | 12 | 0.3 |
| —□— | 23 | 8 | 0.1 | —□— | 25 | 8 | 0.1 |
| —◇— | 23 | 12 | 0.1 | —◇— | 25 | 12 | 0.1 |
| —■— | 23 | 8 | 0.3 | —■— | 25 | 8 | 0.3 |
| —◆— | 23 | 12 | 0.3 | —◆— | 25 | 12 | 0.3 |
| —●— | 21 | 10 | 0.2 | —●— | 23 | 10 | 0.2 |

B. Perfusion Cultures

Figure 3:
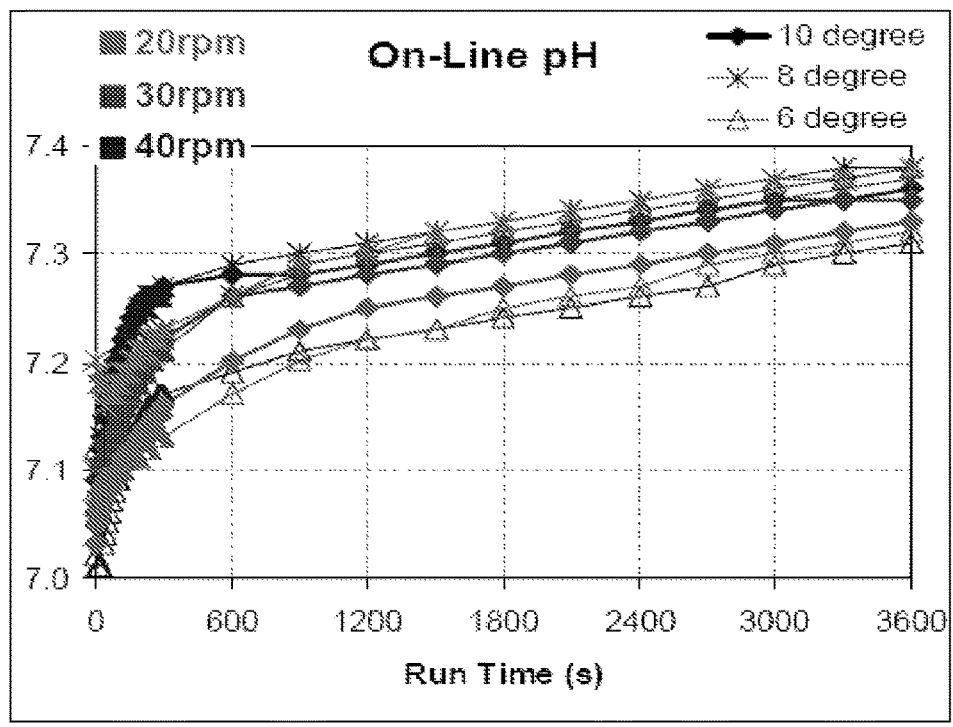
FIG. 3 shows cell-free studies to assess rate of $CO_2$ stripping in the WAVE BIOREACTOR™. (Panel A); raw pH rise data for different rock angle, rock rate with a constant gas flow rate of 0.2 LPM; (Panel B) raw pH rise time-course data for two different rocking set points with different gas flow rates. (Panel C) calculated rate of change in pH for different rocking conditions shown in Panel A; (Panel D) calculated rate of change of pH for the different rocking conditions and different gas flow rates shown in Panel B. The solid bars are the rate of change in pH for the first 5 minutes and the open bars are the calculated rate of change in pH for the next 55 minutes.
Figure 3:
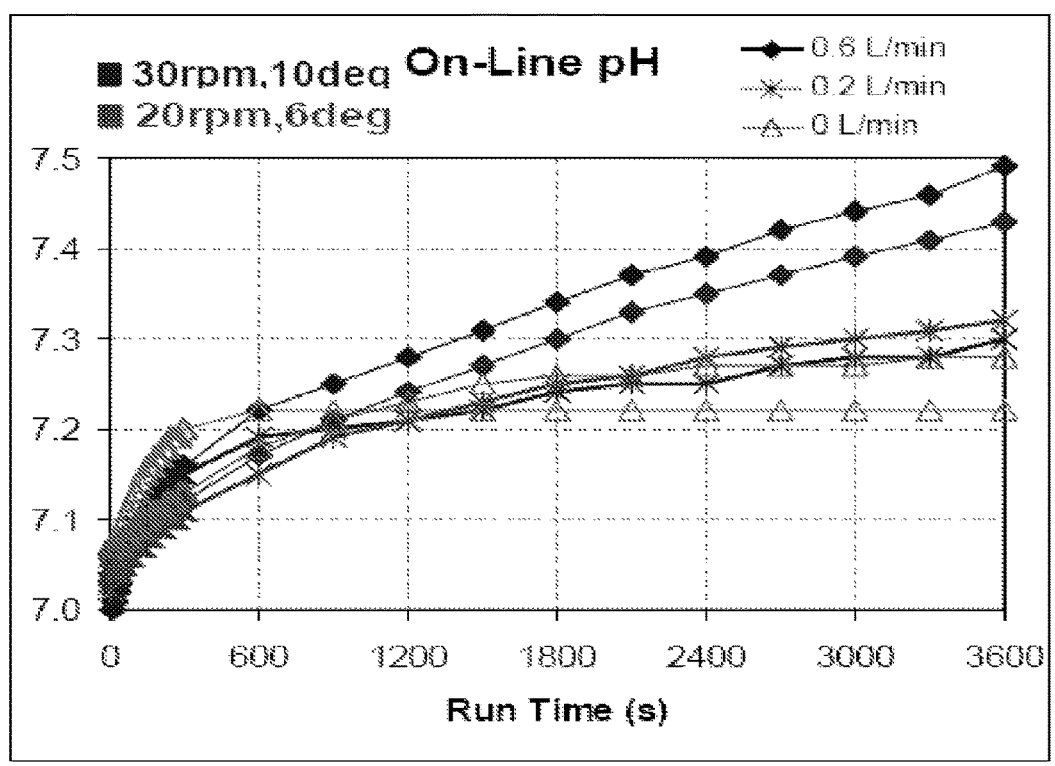
Figure 3:
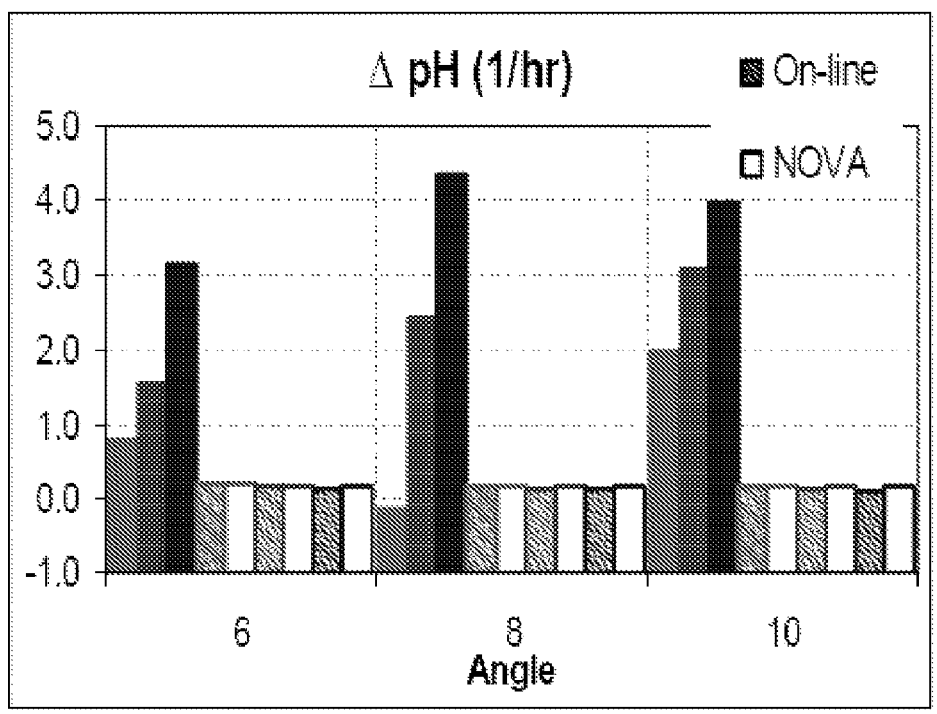
Figure 3:
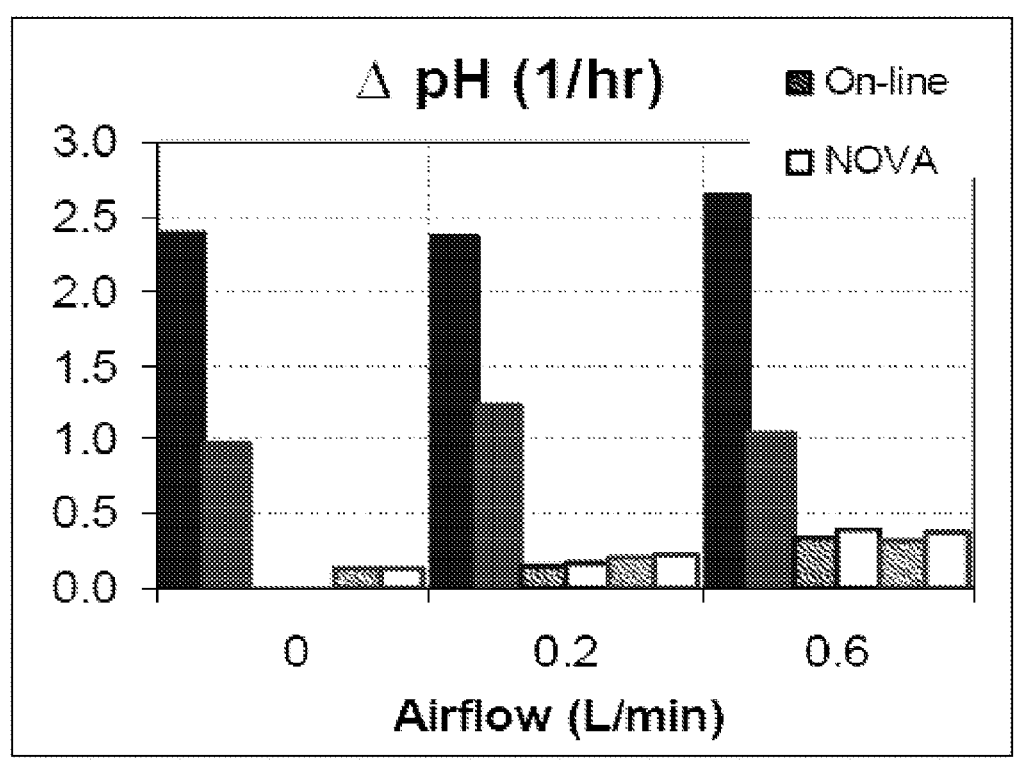
Figure 5:
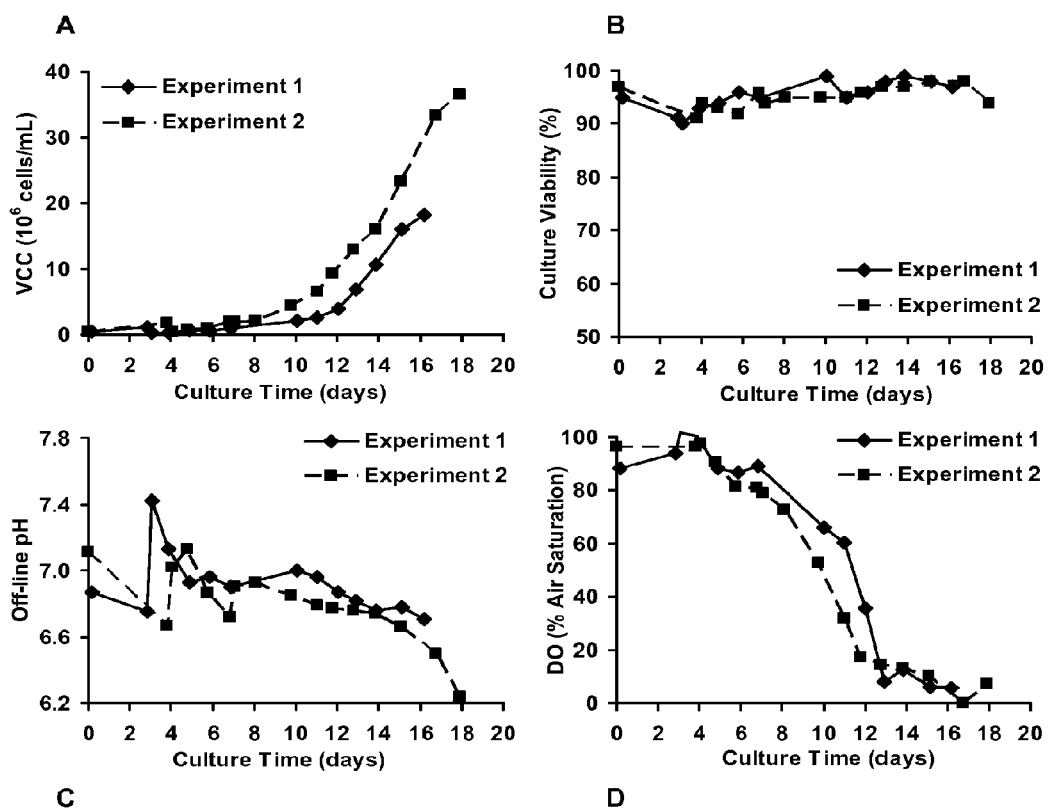
FIG. 5 shows (Panel A) VCC, (Panel B) culture viability (Panel C) off-line pH, and (Panel D) DO concentration for two WAVE BIOREACTOR™ perfusion cultures using cell line producing MAb A run under non-optimized conditions. The cells were cultured in batch mode for the first 6 days and in perfusion mode thereafter. During the batch culture, the working volume in the CELLBAG™ was first inoculated with 6 L of culture, and on day 3, this culture volume was increased to 25 L by the addition of fresh medium. During the perfusion culture, the culture volume was maintained at 25 L at perfusion rate of 1 volume per day. For this set of experiments, the rock rate was 18 rpm and the rock angle was 8 degrees, while the rate of air flow into the headspace was 0.2 L/min. This air was supplemented with 5% CO$_2$ (v/v) for the entire duration of the culture.

In our initial attempts at perfusion culture in the WAVE BIOREACTOR™, culture pH typically dropped below 6.8 and DO often dropped below 30% of air saturation after the onset of perfusion on day 6 (FIG. 5). To minimize the pH drop without increasing perfusion rate, we investigated the feasibility of increasing the air flow rate into the CELLBAG™ because the cell-free gas transfer studies showed that increased air flow rate increased pH (FIG. 3). To overcome the DO decline, we supplemented the air flow into the CELLBAG™ with 30% $O_2$ (v/v) two days after the initiation of perfusion. We selected this timing because it coincided with the previously observed DO decline (FIG. 5).

Example 4: A Batch-Perfusion Process

Figure 7:
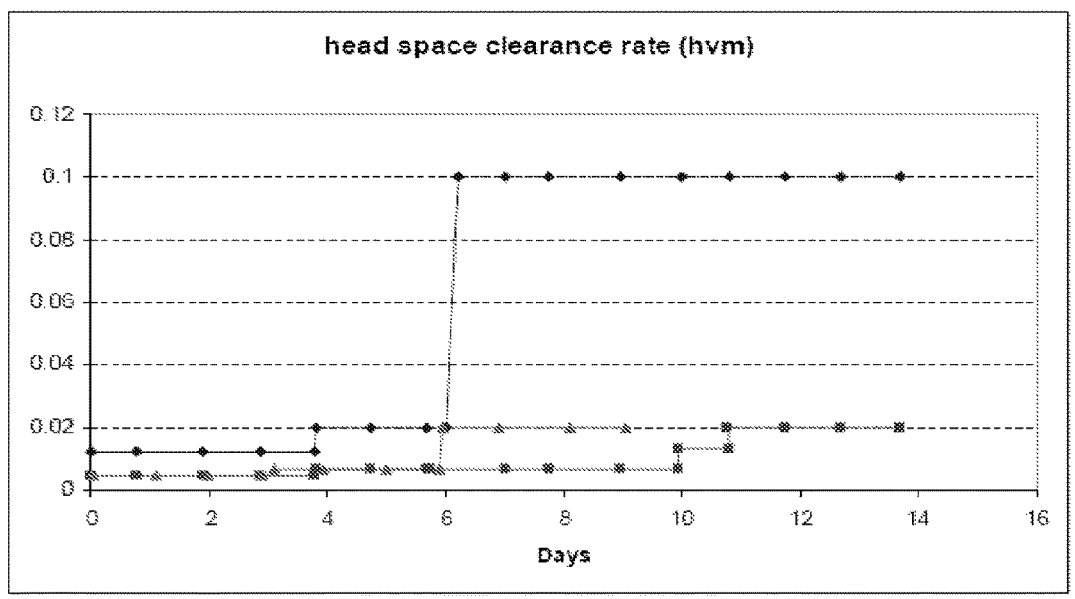
FIG. 7 shows the culture performance from varying head space clearance rates (hvm). (Panel A) shows 2 experiments with one step increase in airflow effecting an increase in head space clearance rate (0.1 hvm in (♦) and 0.02 hvm (-▲-). The other head space clearance rate strategy is many step increases (0.007 hvm to 0.013 hvm to 0.02 hvm) (-■-) on days 10 and 11. (Panel B) the dissolved CO$_2$ partial pressure measured by NOVA BIOPROFILE® 400.
Figure 7:
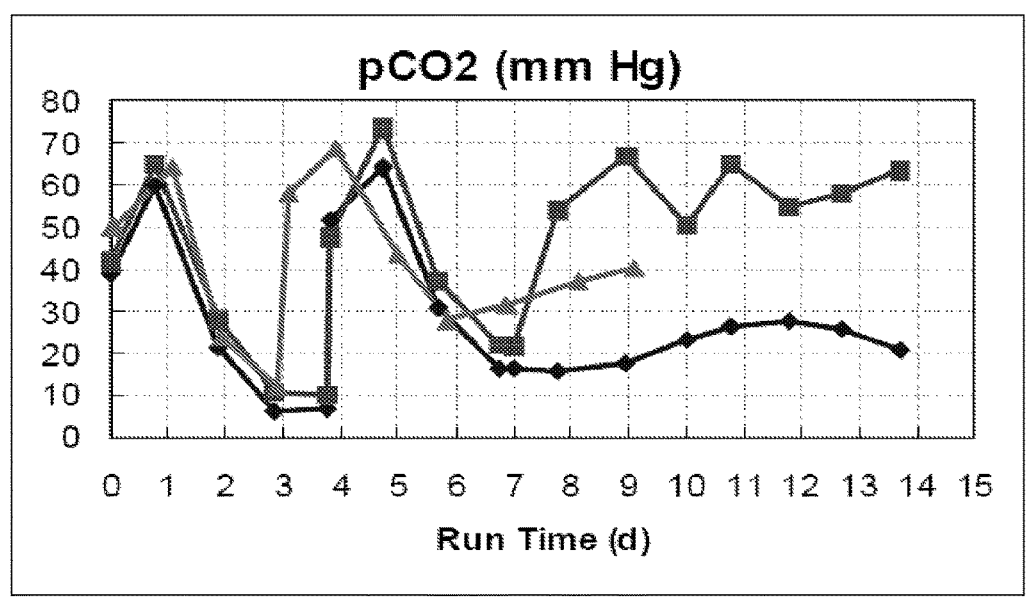

This perfusion process was comprised of two batch steps followed by a perfusion step. A 50 L disposable bag was inoculated at a 6 L working volume at a target cell density of 5 to $7.5 \times 10^5$ cells/mL at the inoculation step. Three days after the inoculation, fresh media was added to increase the volume of the disposable bag to 20 L for the scale-up step. The inoculation step and the scale-up step made up the batch steps. The $CO_2$ step-down strategy for the batch steps was employed as described in the Batch Process. At the end of the 3-day scale-up step, the perfusion was started. Fresh medium was continuously added to the disposable bag and spent culture medium was continuously removed from the disposable bag while retaining the cells. The cell culture medium was perfused at a rate of 20 liters per day (1 volume per day). The perfusion media pH set point was 7.2 units. At the onset of perfusion, $CO_2$ concentration in the incoming gas was set to zero. The head space clearance rate was increased to facilitate $CO_2$ removal. The increase in head space clearance rate either followed a single-step increase or a multi-step increase as shown in FIG. 7. The rocking rate range was between 19 to 25 rpm. The rocking angle range was between 8 and 12 degrees. The temperature was maintained at 37° C. Oxygen was supplemented 48 hours after the onset of perfusion to meet the oxygen demand of the cells. The concentration of oxygen in the incoming gas was set to 30% at 48 hours after the start of perfusion.

Figure 6:
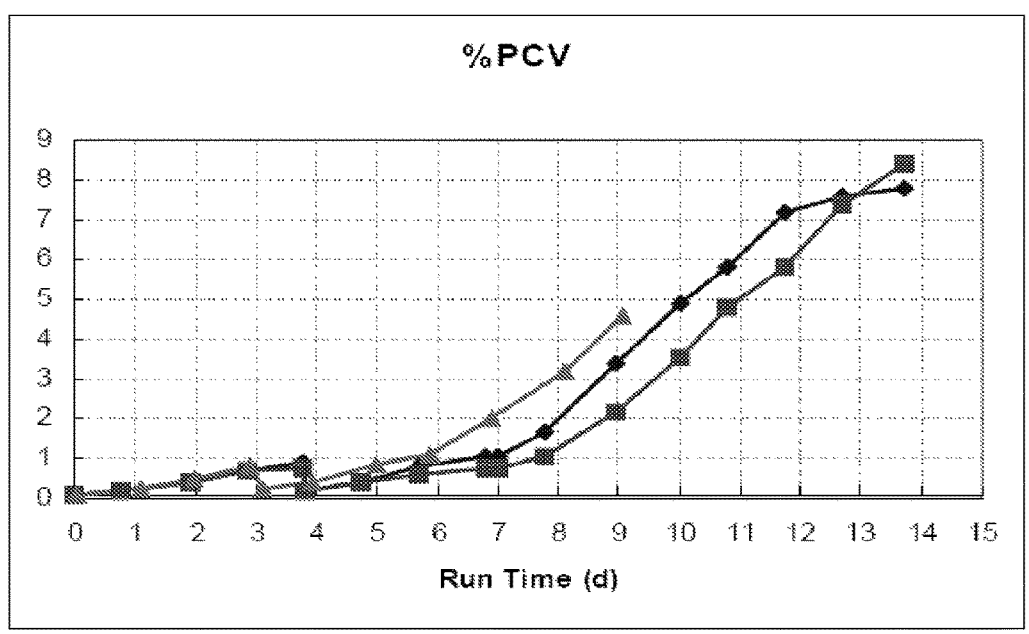
Figure 6:
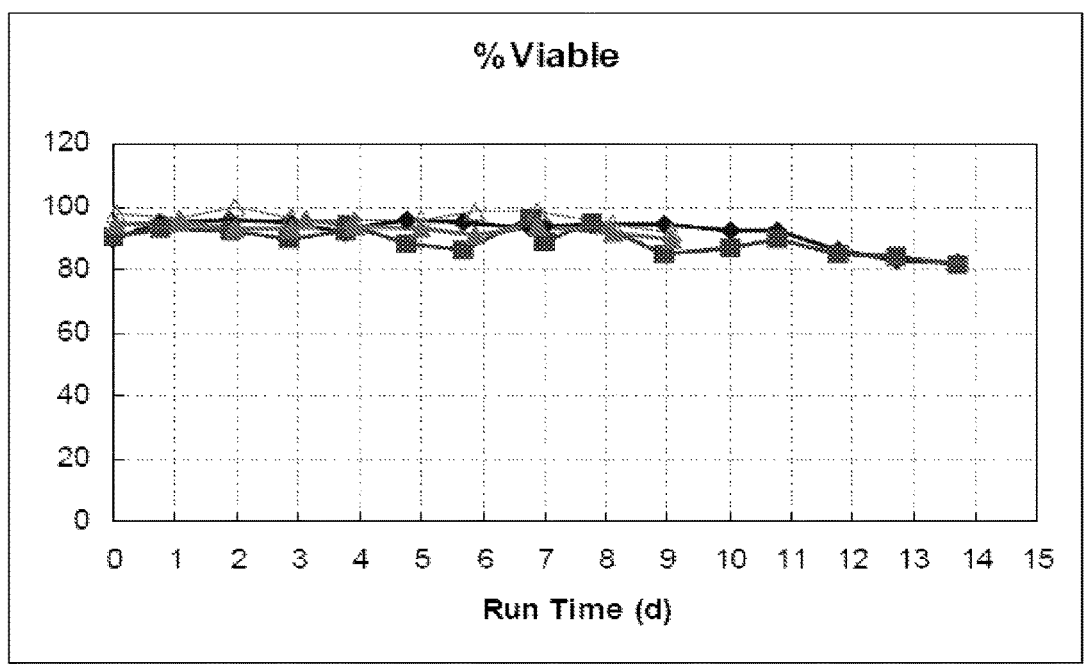
Figure 6:
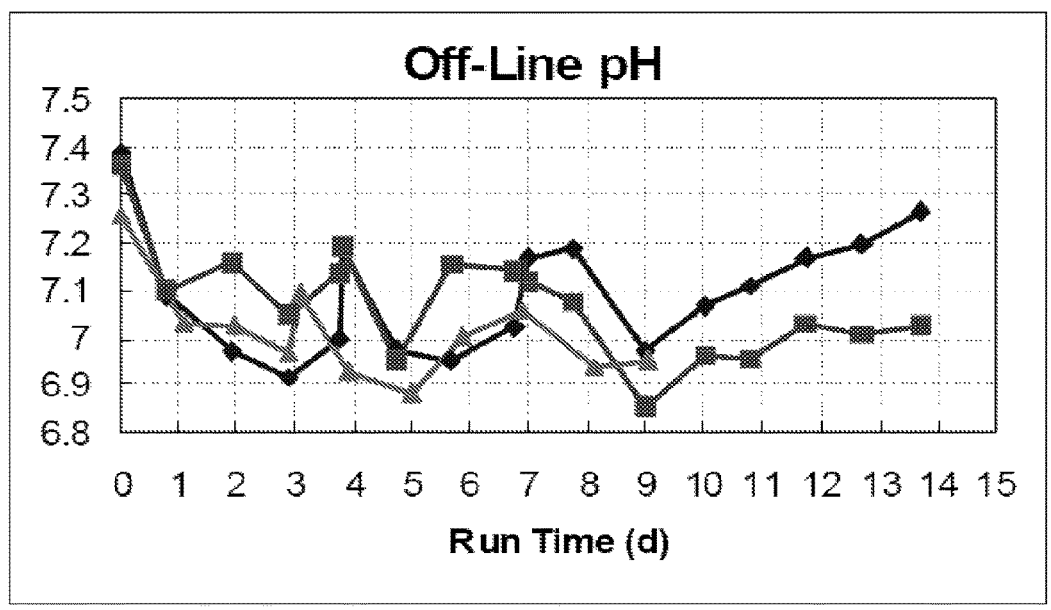
Figure 6:
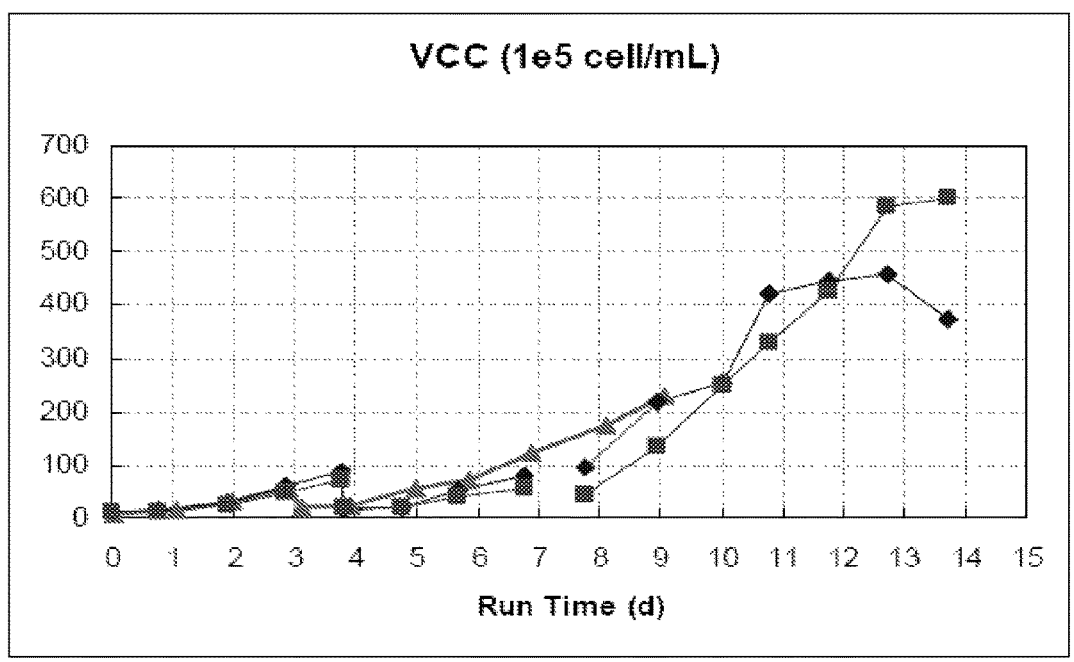

FIG. 6 shows the cell culture performance for the batch-perfusion process (batch step (days 0-6) and perfusion step (days 6-14)) (FIG. 6A). FIG. 6B shows the % cell viability. FIG. 7A shows the head space clearance rate set points for the three different experiments. The head space clearance rate set points for the perfusion step followed different profiles (days 6-14): (1) two constant head space clearance rates: 0.02 hvm (-▲-) and 0.1 hvm (◆); and (2) a step increase of head space clearance rate: 0.007 hvm to 0.013 hvm to 0.02 hvm (-■-). Both single-step increase as well as multi-step increase was studied. FIG. 7B shows the offline dissolved $CO_2$ concentration. FIG. 6D shows cell growth in viable cell count (VCC). Legend for FIGS. 6 and 7: ◆, ■, ▲ show three different runs. As shown in FIG. 6C, pH could be maintained within a desired range by modulating $CO_2$ by clearance of the head space.

Example 5: Behavior of Six CHO Cell Lines Under "8-5-2" Conditions

To test the reliability of this WAVE BIOREACTOR™ process in supporting cell growth and in maintaining pH and DO in the desired ranges, we selected six cell lines that cover the range of cell growth and metabolic behaviors typically observed in our in-house CHO cell lines.

Figure 8:
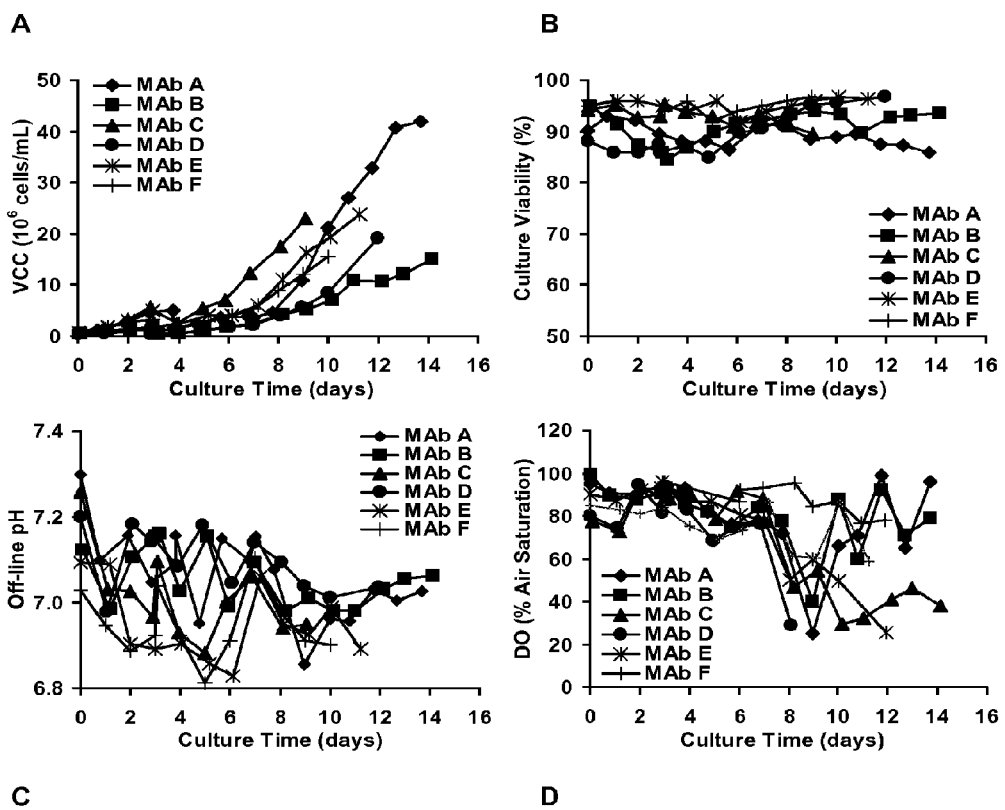
FIG. 8 shows (Panel A) VCC, (Panel B) culture viability (Panel C) off-line pH, and (Panel D) DO for WAVE BIOREACTOR™ cultures of six different cell lines—each producing a different MAb—using the optimized process. During the 6 L inoculation stage, the cultures were rocked at 21 rpm, and the rate of air flow rate into the headspace was 0.2 L/min. This air was supplemented with CO$_2$ at 8% (v/v) for the first day, at 5% (v/v) for the second day, and at 2% (v/v) thereafter. This air flow strategy was repeated for the 20 L scale-up stage (day 3-6). During cultivation in 20 L perfusion mode (day 6 onwards), the rate of air flow into the headspace was maintained at 0.6 L/min without CO$_2$ supplementation, while the blend of O$_2$ to air in the inlet gas was increased from 0% (v/v) to 30% (v/v) on day 8, and maintained at 30% (v/v) for the remaining duration of the culture. The 20 L batch and perfusion cultures were rocked at 23 rpm. The rock angle for all cultures was constant at 10°.

With the optimized process conditions, all six cell lines grew with high viabilities throughout the batch and perfusion culture stages (FIG. 8). In all cases, pH remained within in the desired 6.8-7.2 range, and DO exceeded 20% of air saturation.

Figure 9:
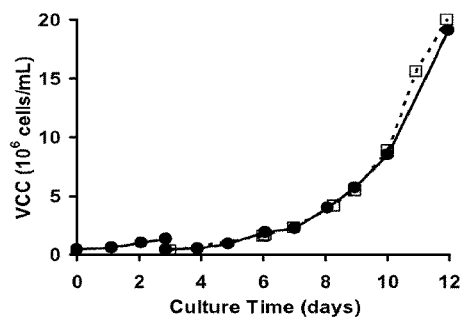
FIG. 9 shows (Panel A) VCC, (Panel B) viability, (Panel C) off-line pH, and (Panel D) off-line DO for parallel cultures of cell line producing MAb E in WAVE BIOREACTOR™ (●) and stirred-tank bioreactor (□).
Figure 9:
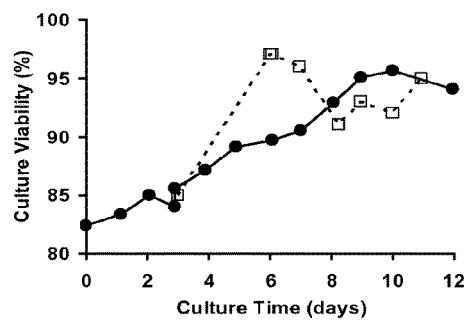
Figure 9:
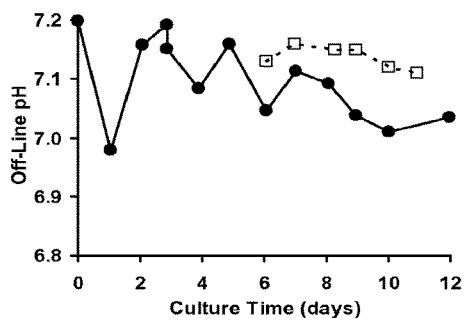
Figure 9:
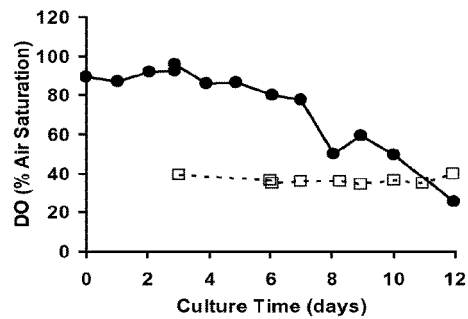

Example 6: Comparison Between the "8-5-2" WAVE BIOREACTOR™ Method and Conventional Stirred-Tank Bioreactor Cultures To compare culture performance between the invention's WAVE BIOREACTOR™ process and the stirred tank bioreactor process with pH and DO control, we conducted parallel cultures in both systems (FIG. 9). The growth and viability profiles were similar between the two bioreactor systems: the growth rates in the WAVE Bioreactor™ and in the stirred tank bioreactor were comparable at ~0.5 day$^{-1}$. Despite the lack of online feedback control for pH and DO in the WAVE BIOREACTOR™ system, the pH and DO profiles did not differ significantly between the two bioreactor cultures.

The invention provides a process control method for maintaining culture pH in the 6.8-7.2 range, and DO>20% of air saturation in the WAVE BIOREACTOR™ system—operated in both batch and perfusion modes—without relying on pH and DO feedback control. After identifying challenges in culturing CHO cells in the WAVE BIOREACTOR™ system without pH and DO control, we conducted cell-free studies to determine the effects of rock rate, rock angle, and gas flow rate on $O_2$ and $CO_2$ transfer in the WAVE BIOREACTOR™ system. By adjusting these process parameters along with the concentration of $CO_2$ and $O_2$ in the inlet gas, we maintained culture pH and DO within our desired range for batch and perfusion cultures of six recombinant CHO cell lines. By eliminating the need for pH and DO probes, this process provides a simpler and more cost-effective method for culturing cells in the WAVE BIOREACTOR™ system. It also provides an alternative method for culturing cells in the event of pH or DO probe failure in WAVE BIOREACTORs™ equipped with these probes.

It is also to be understood that the specific examples described herein are illustrative only and not intended to limit the scope of the invention. The invention is limited only by the appended claims.

REFERENCES CITED

Cronin C N, Lim K B, Rogers J. 2007. Production of selenomethionyl-derivatized proteins in baculovirus-infected insect cells. Protein Sci 16: 2023-2029.
Dunn I J, Einsele A J. 1975. Oxygen transfer coefficients by the dynamic model. J Appl Chem Biotechnol 25: 707-720.
deZengotita V M, Schmelzer A E, Miller W M. 2002. Characterization of hybridoma cell responses to elevated $pCO_2$ and osmolality: Intracellular pH, cell size, apoptosis, and metabolism. Biotechnol Bioeng 77: 369-380.
Haldankar R, Li D, Saremi Z, Baikalov C, Deshpande R. 2006. Serum-free suspension large-scale transient transfection of CHO cells in WAVE bioreactors. Mol Biotechnol 34: 191-199.
Johnson M, Lanthier S, Massie B, Lefebvre G and Kamen A. 1996. Use of the Centritech lab centrifuge for perfusion culture of hybridoma cells in protein-free medium. Biotech Prog 12: 855-864.
Langheinrich C and Nienow A W. 1999. Control of pH in large-scale, free suspension animal cell bioreactors: Alkali addition and pH excursions. Biotechnol Bioeng 66: 171-179.
Lin A, Kimura R, Miller W M. 1993. Production of tPA in recombinant CHO cells under oxygen-limited conditions. Biotechnol Bioeng 42: 339-350.
Ling W L W, Deng L, Lepore J, Cutler C, Connon-Carlson S, Wang Y, Voloch M. 2003. Improvement of monoclonal antibody production in hybridoma cells by dimethyl sulfoxide. Biotechnol Prog 19: 158-162.
Link T, Bäckström M, Graham R, Essers R, Zorner K, G ätgens J, Burchell J, Taylor-Papadimitriou J, Hansson G C, Noll T. 2004. Bioprocess development for the production of a recombinant MUC1 fusion protein expressed by CHO-K1 cells in protein-free medium. J Biotechnol 110: 51-62.
Miller W M, Blanch H W, Wilke C R. 1988. A kinetic analysis of hybridoma growth and metabolism in batch and continuous suspension culture: Effect of nutrient concentration, dilution rate, and pH. Biotechnol Bioeng 32: 947-965.
Mikola M, Seto J, Amanullah A. 2007. Evaluation of a novel Wave Bioreactor cellbag for aerobic yeast cultivation. Bioprocess Biosyst Eng 30: 231-241.
Osman J J, Birch J, Varley J. 2001. The response of GS-NS0 myeloma cells to pH shifts and pH perturbations. Biotechnol Bioeng 75: 63-73.
Osman J J, Birch J, Varley J. 2002. The response of GS-NS0 myeloma cells to single and multiple pH perturbations. Biotechnol Bioeng 79: 398-407.
Rao G, Moreira A, Brorson K. 2009. Disposable bioprocessing: the future has arrived. Biotechnol Bioeng 102: 348-356.
Restelli V, Wang M D, Huzel N, Ethier M, Perreault H, Butler M. 2006. The effect of dissolved oxygen on the production and glycosylation profile of recombinant human erythropoietin produced from CHO cells. Biotechnol Bioeng 94: 481-494.
Royce P N C, Thornhill N F. 1991. Estimation of dissolved carbon dioxide concentrations in aerobic fermentations. AIChE J 37L 1680-1686.
Singh V. 1999. Disposable bioreactor for cell culture using wave-induced agitation. Cytotechnology 30: 149-158.
Tang Y J, Ohashi R, Hamel J F P. 2007. Perfusion culture of hybridoma cells for hyperproduction of $IgG_{2a}$ monoclonal antibody in a Wave bioreactor-perfusion culture system. Biotechnol Prog 23: 255-264.

What is claimed is:
1. A method for culturing Chinese hamster ovary (CHO) cells comprising:
 (i) providing cell culture inoculant comprising CHO cells in about 6 L of a bicarbonate-containing culture liquid to a vessel to achieve a target cell density of about 7.5×10$^5$ CHO cells/mL, wherein said vessel has a volume of about 50 L and has walls that encapsulate said cell culture and a gas phase head space above said cell culture, and wherein said vessel comprises at least one port that provides an entrance and an egress of gas to and from said head space;
 (ii) providing gas to said head space through said port, wherein said gas contains $CO_2$ in an amount of 8% (v/v) of said gas on day 1, in an amount of 5% (v/v) of said gas on day 2, and in an amount of 2% (v/v) of said gas thereafter, thereby modulating the pH of said cell culture to maintain the pH of the culture between pH 6.8 and 7.2;
 (iii) providing fresh culture medium to said vessel to achieve a volume of about 20 L;
 (iv) providing gas to said head space through said port, wherein said gas contains $CO_2$ in an amount of 8%

(v/v) of said gas on day 1, in an amount of 5% (v/v) of said gas on day 2, and in an amount of 2% (v/v) of said gas thereafter, thereby modulating the pH of said cell culture to maintain the pH of the culture between pH 6.8 and 7.2;
(v) perfusing fresh culture medium into said vessel and removing spent culture medium from said vessel at a perfusion rate of about 1 volume per day; and
(vi) providing gas to said head space through said port to sweep accumulated $CO_2$ from the head space of the vessel, wherein said gas contains $O_2$ in an amount of 30% (v/v) of said gas 48 hours after the start of perfusion, thereby maintaining dissolved $O_2$ to a level greater than 20% of air saturation,
wherein the fresh culture medium has a pH of 7.2, the clearance rate of the head space is between 0.002 and 0.1 head space volume per minute (hvm), the vessel is agitated by rocking the vessel at a rock rate between 15 and 30 rocks per minute (rpm) at a rock angle of between 5° and 15°, and wherein the method does not require monitoring and feedback control of pH and dissolved $O_2$.

2. The method of claim 1, wherein the rock rate is between 19 and 25 rpm and the rock angle is between 8° to 12°.

3. The method of claim 1, wherein the clearance rate is between 0.01 to 0.04 hvm.

4. The method of claim 3 wherein the clearance rate is about 0.02 hvm.

5. The method of claim 1 wherein said vessel is a rigid container.

6. The method of claim 1 wherein said vessel is a pliable container.

7. The method of claim 6 wherein said vessel is a disposable culture bag.

8. The method of claim 1 further comprising continuously or intermittently monitoring the pH of the cell culture.

9. The method of claim 1 wherein the perfusion of said fresh culture medium is performed through a perfusion device that allows retention of cells in the vessel.

10. The method of claim 1 wherein said gas is provided to said head space such that the cell culture maintains a partial pressure of dissolved $CO_2$ at a level of about 1 to 200 mmHg.

11. The method of claim 10 wherein said gas is provided to said head space such that the cell culture maintains a partial pressure of dissolved $CO_2$ at a level of about 10 to 150 mmHg.

12. The method of claim 11 wherein said gas is provided to said head space such that the cell culture maintains a partial pressure of dissolved $CO_2$ at a level of about 20 to 120 mmHg.

13. The method of claim 12 wherein said gas is provided to said head space such that the cell culture maintains a partial pressure of dissolved $CO_2$ at a level of about 20 to 80 mmHg.

14. The method of claim 1, wherein the gas flow rate is 0.2 L/min on day 0 to day 3, 0.4 L/min on day 3 to day 6, and 0.6 L/min on day 6 and thereafter.

15. The method of claim 1, wherein the gas flow rate is 0.6 L/min.

16. The method of claim 1, wherein the gas flow rate is 1.0 L/min.

* * * * *